United States Patent
Huang et al.

(10) Patent No.: US 10,925,480 B2
(45) Date of Patent: Feb. 23, 2021

(54) OPTICAL COHERENCE TOMOGRAPHY ANGIOGRAPHY METHODS

(71) Applicants: David Huang, Portland, OR (US); Yali Jia, Portland, OR (US)

(72) Inventors: David Huang, Portland, OR (US); Yali Jia, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 315 days.

(21) Appl. No.: 16/000,824

(22) Filed: Jun. 5, 2018

(65) Prior Publication Data

US 2018/0344147 A1 Dec. 6, 2018

Related U.S. Application Data

(63) Continuation of application No. 15/080,471, filed on Mar. 24, 2016, now abandoned.

(60) Provisional application No. 62/138,196, filed on Mar. 25, 2015.

(51) Int. Cl.
| | |
|---|---|
| *G06K 9/00* | (2006.01) |
| *A61B 3/00* | (2006.01) |
| *A61B 3/10* | (2006.01) |
| *A61B 3/12* | (2006.01) |
| *A61B 3/14* | (2006.01) |

(52) U.S. Cl.
CPC ......... *A61B 3/0025* (2013.01); *A61B 3/0041* (2013.01); *A61B 3/102* (2013.01); *A61B 3/1233* (2013.01); *A61B 3/1241* (2013.01); *A61B 3/14* (2013.01); *G06T 2207/30041* (2013.01)

(58) Field of Classification Search
CPC ..... A61B 3/0025; A61B 3/0041; A61B 3/102; A61B 3/1233; A61B 3/1241; A61B 3/14; G06T 2207/30041
See application file for complete search history.

(56) References Cited

U.S. PATENT DOCUMENTS

| | | | |
|---|---|---|---|
| 9,226,654 B2 * | 1/2016 | Sadda | G06T 7/0012 |
| 9,357,916 B2 * | 6/2016 | Srivastava | G06T 7/215 |
| 2007/0115481 A1 * | 5/2007 | Toth | A61B 3/0025 |
| | | | 356/511 |
| 2014/0073917 A1 | 3/2014 | Huang et al. | |

OTHER PUBLICATIONS

Jia, Yali, et al. "Quantitative optical coherence tomography angiography of choroidal neovascularization in age-related macular degeneration." Ophthalmology 121.7 (Jul. 1, 2014): 1435-1444.*

* cited by examiner

*Primary Examiner* — Shefali D Goradia

(74) *Attorney, Agent, or Firm* — Schwabe, Williamson & Wyatt, P.C.

(57) ABSTRACT

Methods of applying OCT angiography are disclosed. In particular, methods of detecting, visualizing and measuring the extent of retinal neovascularization are disclosed. Further disclosed are methods measuring retinal nonperfusion area and choriocapillaris defect area.

16 Claims, 38 Drawing Sheets

OPTICAL COHERENCE TOMOGRAPHY ANGIOGRAPHY METHODS

CROSS REFERENCE TO RELATED APPLICATIONS

The present application is a Continuation Application of application Ser. No. 15/080,471, filed Mar. 24, 2016, entitled "OPTICAL COHERENCE TOMOGRAPHY ANGIOGRAPHY METHODS," and which claims priority to U.S. Provisional Patent Application No. 62/138,196 filed Mar. 25, 2015, both of which are hereby incorporated by reference.

ACKNOWLEDGEMENT OF GOVERNMENT SUPPORT

This invention was made with the support of the United States government under the terms of grant numbers R01 EY013516 and R01 EY023285 awarded by the National Institutes of Health. The United States government has certain rights to this invention.

FIELD

Generally, the field involves methods of using optical coherence tomography (OCT) in angiography. More specifically, the field involves methods of processing OCT angiography images.

BACKGROUND

Retinal vascular diseases are a leading cause of blindness. Optical coherence tomography (OCT) has become the standard imaging modality in ophthalmology for evaluating fluid accumulation in these diseases and guiding treatment. OCT provides cross-sectional and three-dimensional (3D) imaging of the retina and optic nerve head with micrometer-scale depth resolution. Structural OCT enhances the clinician's ability to detect and monitor fluid exudation associated with retinal vascular diseases. While anatomical alterations that impact vision are readily visible, structural OCT has a limited ability to image the retinal or choroidal vasculatures. Furthermore, it is unable to directly detect capillary dropout or pathologic new vessel growth (neovascularization) that are the major vascular changes associated with two of the leading causes of blindness, age-related macular degeneration (AMD) and diabetic retinopathy. To visualize these changes, traditional intravenous contrast dye-based angiography techniques are currently used.

Fluorescein dye is primarily used to visualize the retinal vasculature. A separate dye, indocyanine green (ICG), is necessary to evaluate the choroidal vasculature. Both fluorescein angiography (FA) and ICG angiography require intravenous injection, which is time consuming, can cause nausea, vomiting, and, rarely, anaphylaxis (Lopez-Saez M P et al, *Ann Allergy Asthma Immunol* 81, 428-430 (1998; incorporated by reference herein). Dye leakage or staining provides information regarding vascular incompetence (e.g., from abnormal capillary growth), but it also obscures the image and blurs the boundaries of neovascularization, making characterization of the shape and extent of such defects unreliable. Additionally, conventional angiography is two-dimensional (2D), which makes it difficult to distinguish vascular abnormalities within different layers. Therefore, it is desirable to develop a non-injection, dye-free method for 3D visualization of ocular circulation.

In recent years, several OCT angiography methods have been developed to detect changes in the OCT signal caused by flowing red blood cells in blood vessels. Initially, Doppler OCT angiography methods were investigated for the visualization and measurement of blood flow (Wang R K et al, *Opt Express* 15, 4083-4097 (2007); Grulkowski I et al, *Opt Express* 17, 23736-23754 (2009); Yu L and Chen Z, J Biomed Opt 15, 016029 (2010); Makita S et al, *Opt Express* 19, 1271-1283 (2011); Zotter S et al, *Opt Express* 19, 1217-1227 (2011); and Braaf B et al, *Opt Express* 20, 20516-20534 (2012)). Because Doppler OCT is only sensitive to motion parallel to the OCT probe beam, it is limited in its ability to image retinal and choroidal circulations, which are predominantly perpendicular to the OCT beam. More recent approaches, based on detecting variation in the speckle pattern over time, are sensitive to both transverse and axial flow. Several types of speckle-based techniques have been described, including amplitude-based (Mariampillai A et al, *Opt Lett* 33, 1530-1532 (2008); Motaghiannezam R and Fraser S, Biomed *Opt Express* 3, 503-521 (2012); and Enfield J et al, *Biomed Opt Express* 2, 1184-1193 (2011); all of which are incorporated by reference herein), phase-based (Fingler J, *Opt Express* 17, 22190-22200 (2009); incorporated by reference herein), or a combination of both amplitude+phase variance methods (Liu G et al, *Biomed Opt Express* 3, 2669-2680 (2012); incorporated by reference herein).

However, using these OCT imaging methods it remains difficult to distinguish the vascular pathologies such as capillary dropout and neovascularization with the retinal and choroidal vasculature using en face projection views and cross sectional views, and quantification of the area of these pathological structures is problematic due to projection artifacts and image noise. Thus, more clinically useful methods for extracting and presenting information derived from structural OCT and OCT angiography data is needed.

SUMMARY

Disclosed herein are systems and methods for OCT angiography segmentation, visualization, and quantification to provide comprehensive information that a clinician could use to assess and manage a variety of ophthalmological pathologies.

Disclosed herein are methods of color coding blood flow in an OCT angiogram. The method involves receiving a set of cross-sectional angiograms, segmenting those cross sectional angiograms into layers, and generating, for example, an en face inner retina angiogram, an en face outer retinal angiogram, and a choroid angiogram. Flow projection artifacts cast by more superficial layers are removed from the en face outer retina angiogram. Neovascularization is detected in the outer retina using pattern recognition, image masks, and thresholding operations. Colors are assigned to flow in the inner retina, choroid, and outer retina. Disclosed herein are methods of removing projection artifacts in an OCT angiogram of the outer retina. These methods involve receiving a set of cross-sectional OCT angiograms, generating en face inner retina angiograms and en face outer retina angiograms, applying a filter to the en face inner retina angiogram, thereby creating a filtered en face inner retina angiogram, generating a binary large inner retinal vessel mask from the filtered en face inner retina angiogram, multiplying each element from the mask matrix with its corresponding element in an outer retina layer matrix generated from the en face outer retina angiogram, and outputting a projection artifact free en face outer retina angiogram.

A similar methodology can also be applied to remove projection artifacts in an OCT angiogram of a choriocapillaris layer as well as an OCT angiogram of a choroid layer.

Disclosed herein are methods of visualizing choroidal neovascularization (CNV) using OCT. These methods involve receiving a set of cross-sectional angiograms, segmenting the set of cross sectional angiograms into layers, generating an en face inner retina angiogram and an en face outer retina angiogram, and removing flow projection artifacts from the en face outer angiogram thereby producing a second en face outer retina angiogram. The methods further involve generating a color coded composite en face outer retina angiogram from the en face inner retina angiogram and the en face outer retina angiogram. The CNV can then be classified by type on the basis of outer retinal flow and position relative to the retinal pigment epithelial (RPE).

Disclosed herein are methods of visualizing retinal neovascularization (RNV) using OCT. These methods involve receiving a set of cross-sectional angiograms, segmenting the set of cross sectional angiograms into layers, generating an en face inner retina angiogram and an en face vitreous angiogram. The methods further involve generating a color coded composite en face angiogram by overlaying the en face inner retina angiogram and the en face vitreous angiogram.

Disclosed herein are methods of measuring the area of CNV and flow index. These methods involve receiving a set of cross-sectional angiograms, segmenting the set of cross sectional angiograms into layers, generating an en face outer retina angiogram, and removing a flow projection artifact from the en face outer retina angiogram, thereby producing a second en face outer retina angiogram, removing background noise using a filter, identifying the CNV using vascular pattern recognition and calculating the CNV area and flow index.

Disclosed herein are methods of measuring the area of RNV and flow index. These methods involve receiving a set of cross-sectional angiograms, segmenting the set of cross sectional angiograms into layers, generating an en face vitreous angiogram, removing background noise from the en face vitreous angiogram using a filter, identifying the RNV using vascular pattern recognition, and calculating the RNV area and flow index.

Disclosed herein are methods of measuring the nonperfusion area of the inner retina. These methods involve receiving a set of cross-sectional angiograms, segmenting the set of cross sectional angiograms into layers, generating an en face inner retina angiogram, thresholding the en face inner retina angiogram to remove pixels that have decorrelation values greater than a cutoff value, removing pixel clusters having an area below a specified value, closing holes within the remaining pixel clusters, and calculating the nonperfusion area. A similar methodology can be used to measure a nonperfusion area or defect area in the choriocapillaris.

It is an object of the invention to distinguish CNV from surrounding outer retinal tissue, hemorrhage, RPE, BM, and non-flow material under (pigment epithelial detachments (PED's.)

It is an object of the invention to provide quantitative assessments of CNV area and flow index that are proportional to average avascular density and flow velocity on the capillary scale.

It is an object of the invention to use OCT angiography to identify foveal avascular zone (FAZ) enlargement and irregularity, capillary drop out, and microaneurysms and neovascularization, particularly in patients with diabetic retinopathy, more accurately than with fluorescein angiography.

It is an object of the invention to provide a comprehensive OCT angiography system that includes scanning, flow detection, segmentation, display, and quantification.

It is an object of the invention to provide a system that is able to capture a large 6×6 mm view of the macula with adequate resolution using a commercially available OCT system.

It is an object of the invention to provide a multicolor display system showing multiple circulations in the same image panel so that the location of pathologies can be located in relation to the retinal vasculature with minimal interference from flow projection artifacts.

It is an object of the invention to provide quantification of RNV and quantification of the area of capillary dropout in the retinal circulation and choriocapillaris.

This Summary is provided to introduce a selection of concepts in a simplified form that are further described below in the Detailed Description. This Summary is not intended to identify key features or essential features of the disclosed subject matter, nor is it intended to be used to limit the scope of the disclosed subject matter. Furthermore, the disclosed subject matter is not limited to implementations that solve any or all disadvantages noted in any part of this disclosure.

Figure 11A:
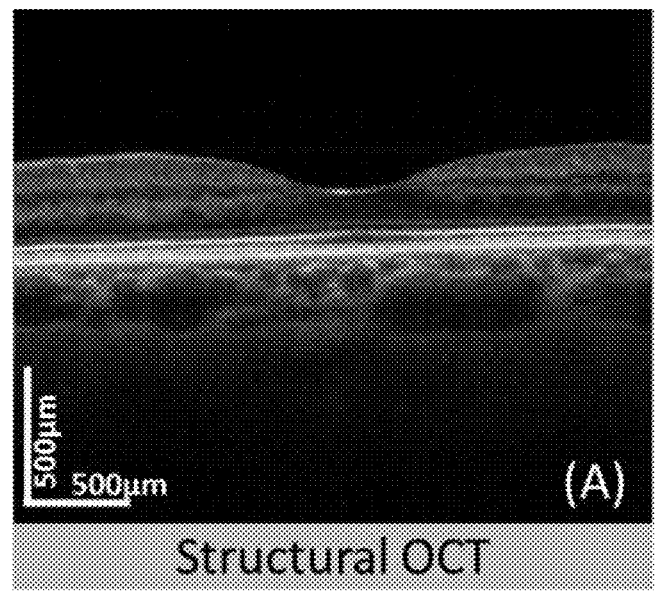
FIG. 11A is a cross sectional OCT reflectance image of a healthy control subject.
Figure 11B:
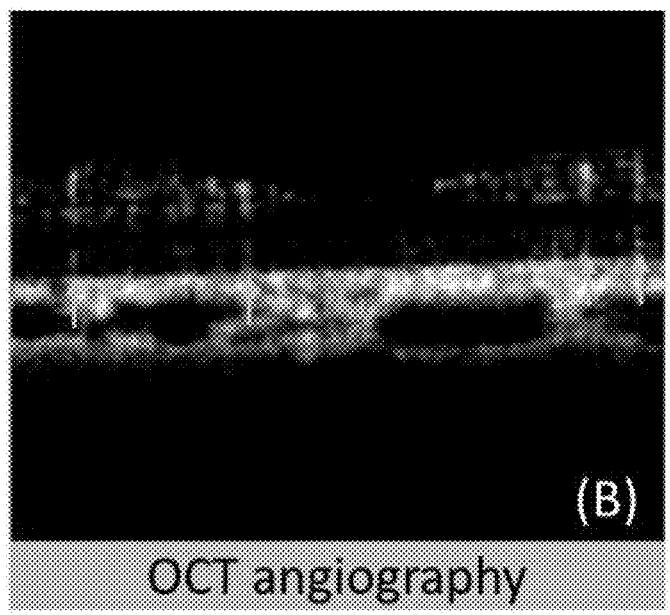
FIG. 11B is a cross sectional OCT angiography image of a healthy control subject. Arrows point to locations where flows in inner retinal vessels are projected onto bright photoreceptor and retinal pigment epithelium layers.
Figure 11C:
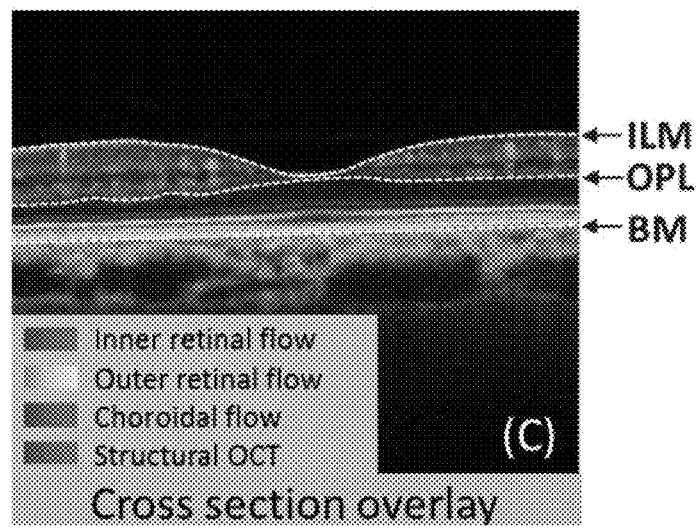
FIG. 11C is a cross sectional color OCT angiogram in a healthy control subject. The internal limiting membrane (ILM) and outer plexiform layer (OPL) and Bruch's membrane (BM) are indicated. They are the boundaries separating inner retinal, outer retinal and choroidal circulations.
Figures 11D, 11E, 11F:
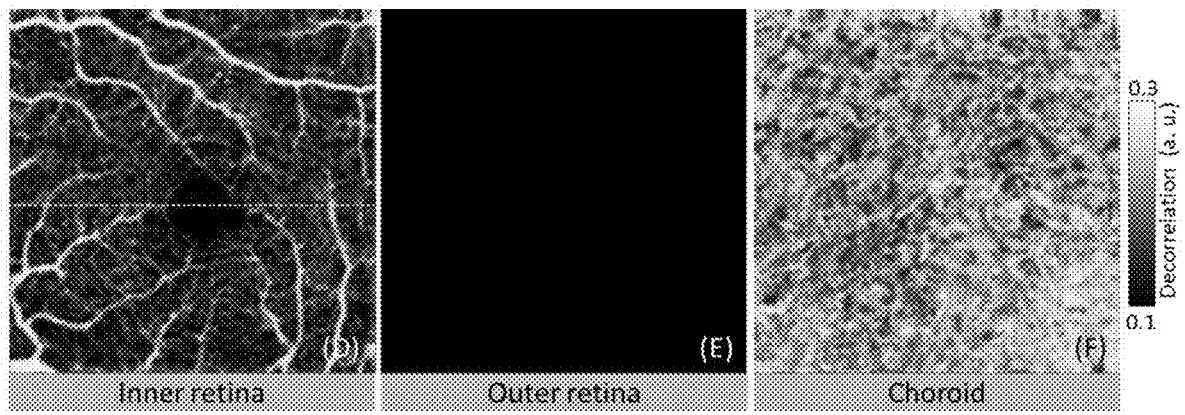
FIG. 11D is an en face angiogram of the inner retina in a healthy control subject. Dashed line indicates the cross sections in Figures A-C above.
FIG. 11E is an en face angiogram of the outer retina in a healthy control subject.
FIG. 11F is an en face angiogram of the choroid in a healthy control subject.

En face angiograms of FIGS. 11D, 11E, and 11F were produced by maximum flow projections within segmented layers and span a 3×3 mm area. A higher decorrelation value (scale to the right of FIG. 11F) corresponds to higher blood flow density.

Figure 12A:
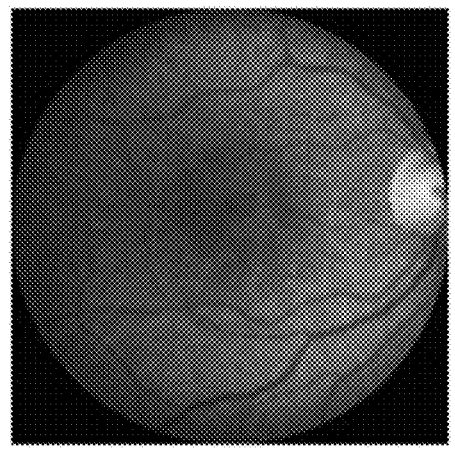

FIG. 12A is a color fundus photograph showing subretinal hemorrhage in a first subject with age-related macular degeneration. The red square outlines the area shown in the angiograms of FIGS. 12B-12I below.

Figure 12B:
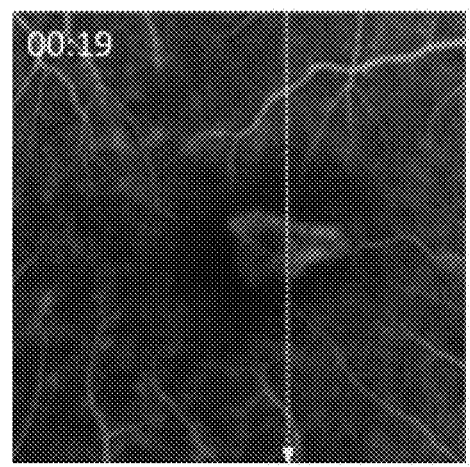

FIG. 12B is an early-phase fluorescein angiography image in the subject.

Figure 12C:
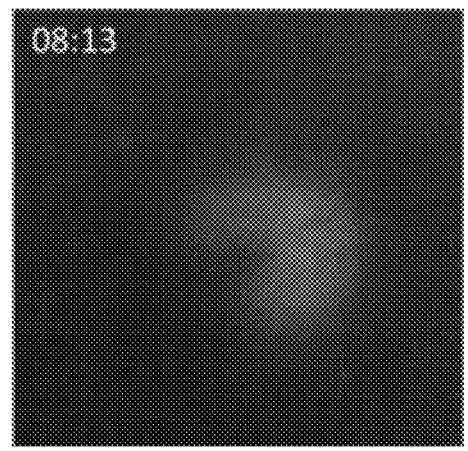

FIG. 12C is an image of late-phase fluorescein angiography in the subject.

Figure 12D:
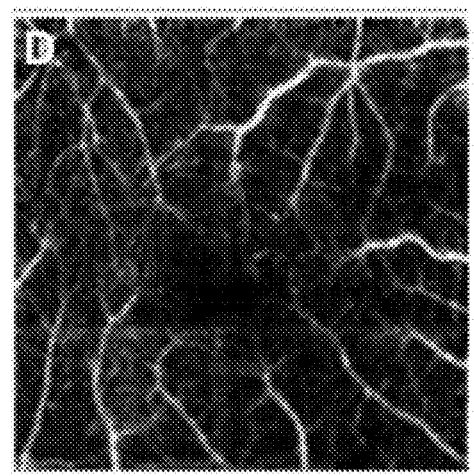

FIG. 12D is an en face optical coherence tomography (OCT) angiogram of the inner retina in the subject.

Figure 12E:
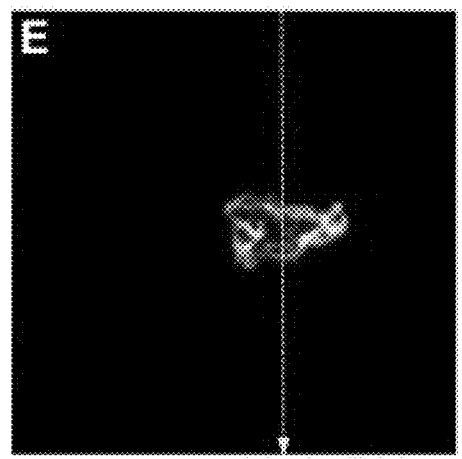

FIG. 12E is an en face OCT angiogram of the outer retina showing the CNV in the subject. The yellow dashed lines indicate the position of OCT cross-section shown in FIG. 12G. Yellow arrows indicate the superior to inferior direction.

Figure 12F:
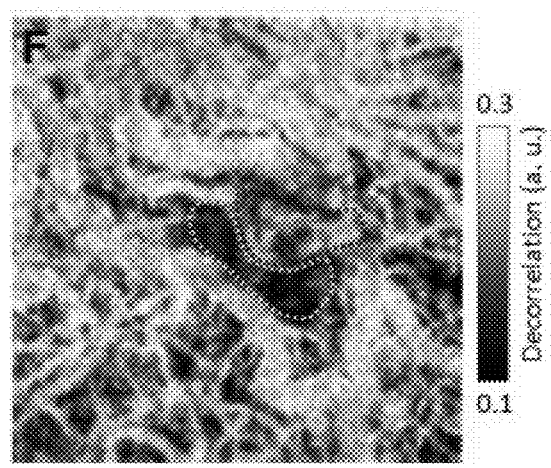

FIG. 12F is an en face angiogram of the choroid in the subject showing patchy flow directly under the CNV (blue dotted outline) and an adjacent area of reduced flow (green dotted outline).

Figure 12G:
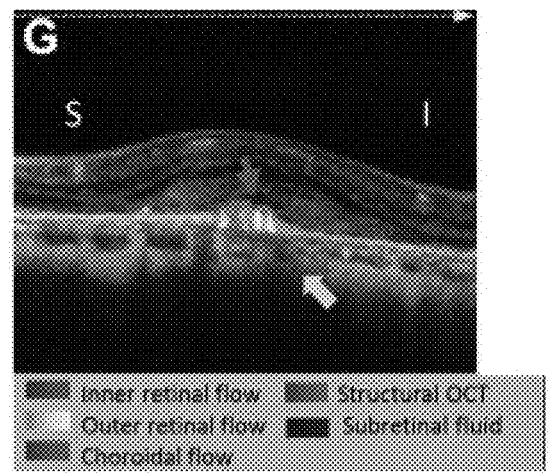

FIG. 12G is a cross-sectional color OCT angiogram in the subject showing the CNV (yellow) was predominantly under the retinal pigment epithelial (RPE). The blue arrow shows the location of the subretinal fluid. The green arrow corresponds to the green dashed outline in F showing a focal region of reduced choroidal flow adjacent to the CNV.

Figure 12H:
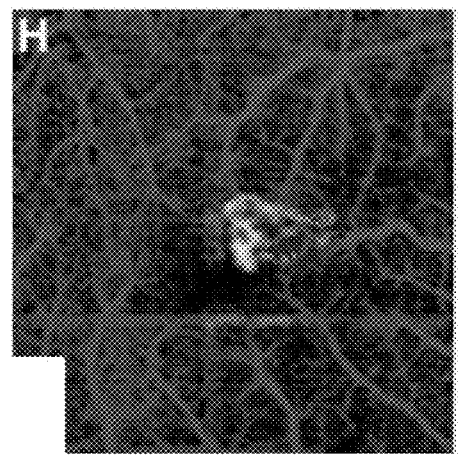

FIG. 12H is a composite en face OCT angiogram in the subject showing most subretinal fluid (dark blue) inferior to the CNV.

Figure 12I:
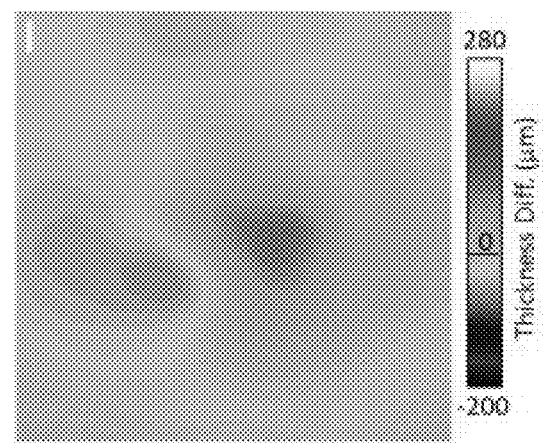

FIG. 12I is a retinal thickness deviation map showing retinal thickening over the CNV in the subject. I=inferior; S=superior.

Figure 13A:
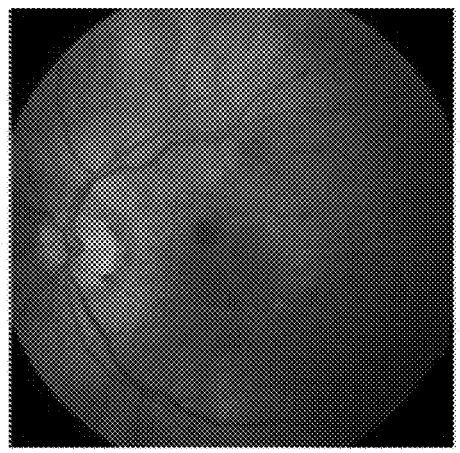

FIG. 13A is a color fundus photograph showing subretinal hemorrhage in a second subject with age related macular degeneration. The red square outlines the area shown in the angiograms of FIGS. 13B-13I below.

Figure 13B:
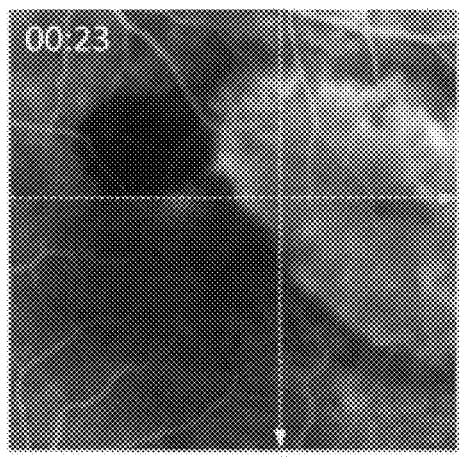

FIG. 13B is an early-phase fluorescein angiography image in the subject.

Figure 13C:
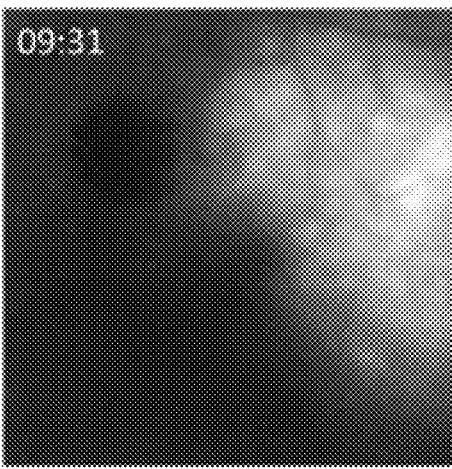

FIG. 13C is an image of late-phase fluorescein angiography in the subject.

Figure 13D:
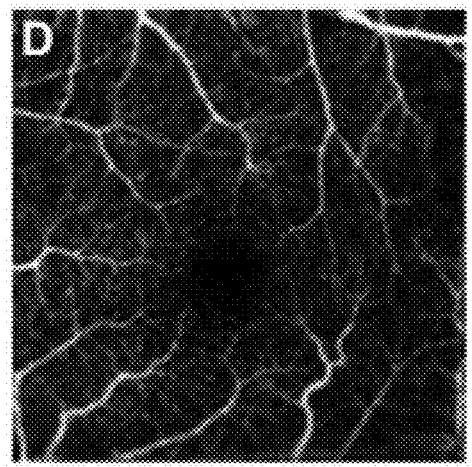

FIG. 13D is an en face optical coherence tomography (OCT) angiogram of the inner retina in the subject.

Figure 13E:
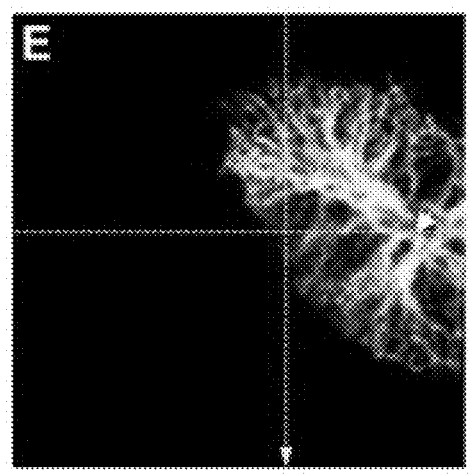

FIG. 13E is an en face OCT angiogram of the outer retina showing the CNV in the subject. The yellow and green dashed lines indicate the position of OCT cross-section shown in FIGS. 13G, 13H, and 13I.

Figure 13F:
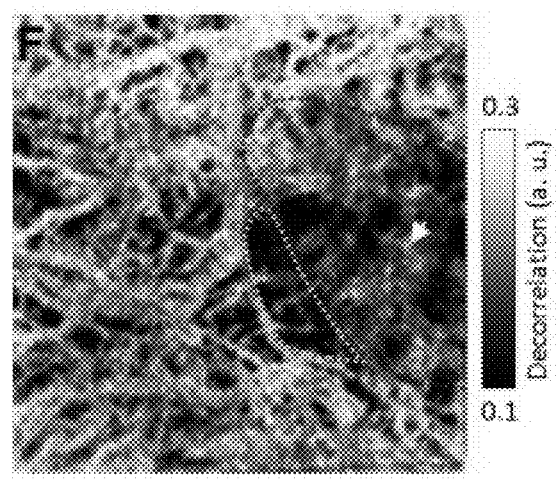

FIG. 13F is an en face angiogram of the choroid showing the patchy reduced flow directly under the CNV (blue dotted outline) and an adjacent area of reduced flow (green dotted outline) in the subject.

Figure 13G:
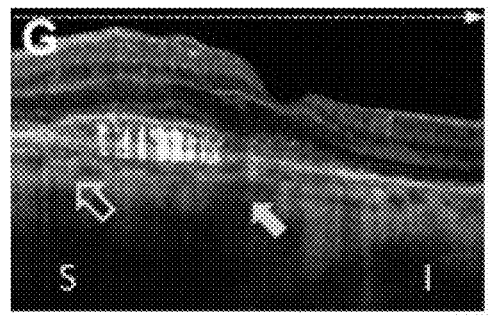
Figure 13G:
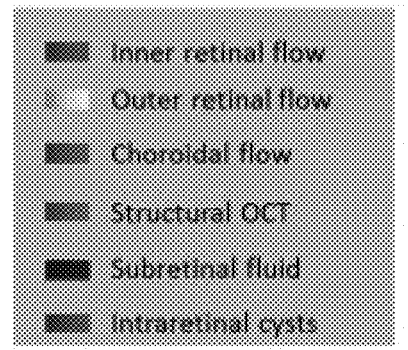

FIG. 13G is a Vertical cross-sectional color OCT angiogram showing the CNV (yellow) was predominantly above the retinal pigment epithelial (RPE) in the subject. The green solid arrow corresponds to the green dotted outline in FIG. 13F showing a focal region of reduced choroidal flow inferonasal to the CNV. The green hollow arrow points out a high choroidal flow signal superior to the CNV.

Figure 13H:
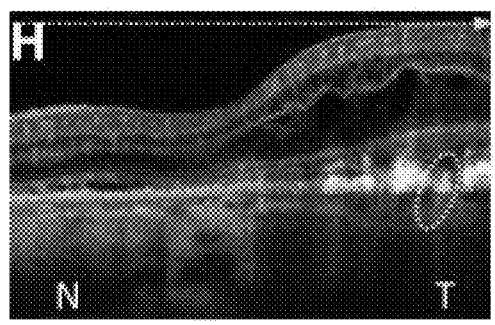

FIG. 13H is a horizontal cross-sectional color OCT angiogram showing the feeder vessel (yellow dotted circle) that corresponds to the white arrows in FIGS. 13E and 13F. Also note cystic intraretinal fluid above the CNV.

Figure 13I:
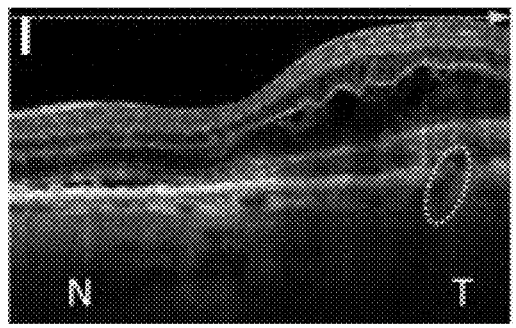

FIG. 13I is a horizontal cross-sectional OCT reflectance image showing the feeder vessel seen as a flow void.

Figure 13J:
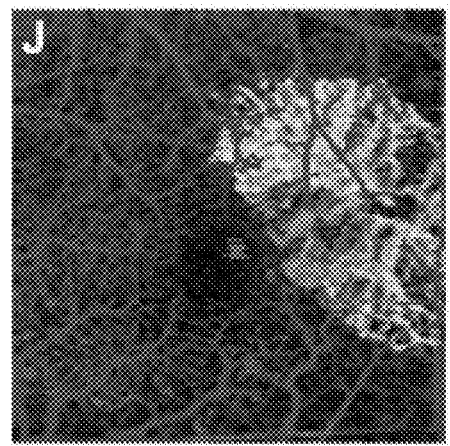

FIG. 13J is a composite en face OCT angiogram showing subretinal fluid (dark blue) at the superonasal corner and intraretinal fluid (light blue) over the CNV.

Figure 13K:
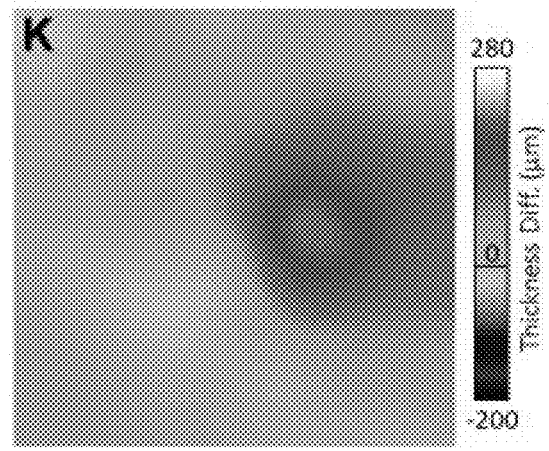

FIG. 13K is a retinal thickness deviation map showing thickening over the CNV in the subject.

Figure 14A:
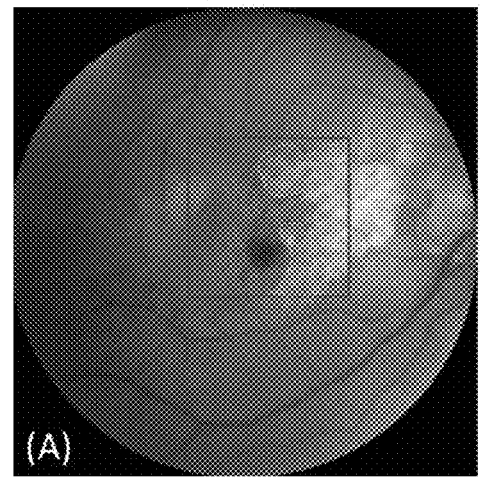

FIG. 14A is a color fundus photograph showing subretinal hemorrhage, retinal pigment epithelium tear, and geographic atrophy (blue dashed outline) in a third subject with age related macular degeneration. The red square outlines indicate the area shown on the angiograms in FIGS. 14B-14I below.

Figure 14B:
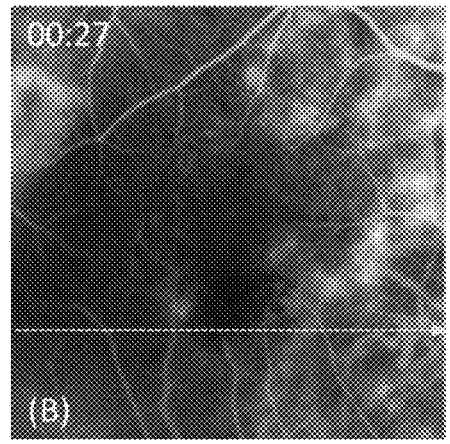

FIG. 14B is an early-phase fluorescein angiography image in the subject.

Figure 14C:
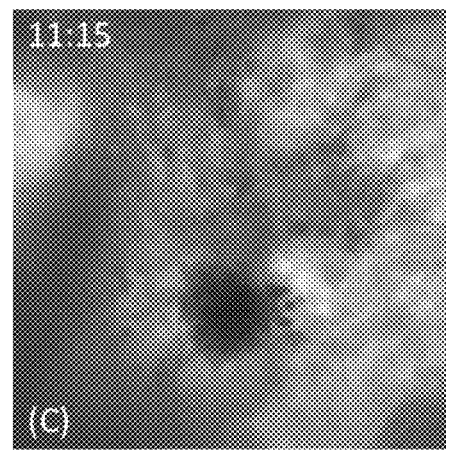

FIG. 14C is an image of late-phase fluorescein angiography in the subject.

Figure 14D:
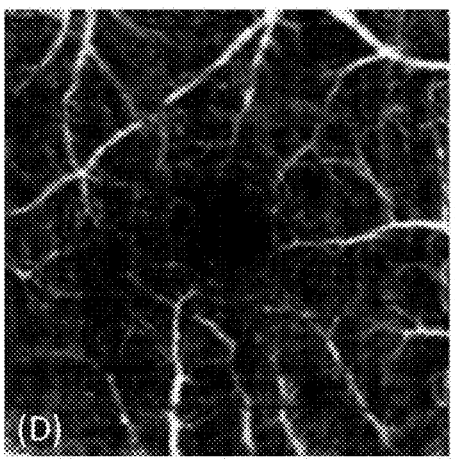

FIG. 14D is an en face OCT angiogram of the inner retina in the subject.

Figure 14E:
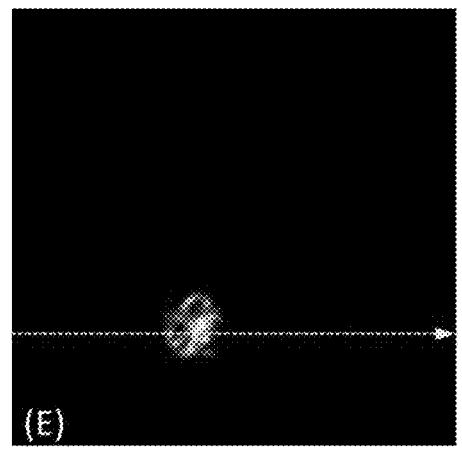

FIG. 14E is an en face angiogram of the outer retina showing the CNV. The yellow dashed lines indicated the position of the OCT cross-section shown in FIG. 14G.

Figure 14F:
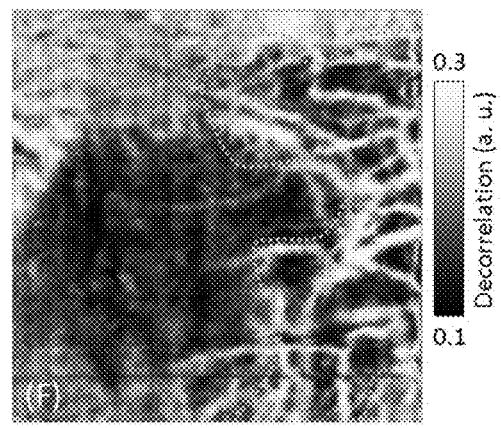

FIG. 14F is an en face angiogram of the choroid showing diffuse reduction of flow signal under the pigment epithelial detachment and choriocapillaris defect in the area of geographic atrophy (blue dashed outline).

Figure 14G:
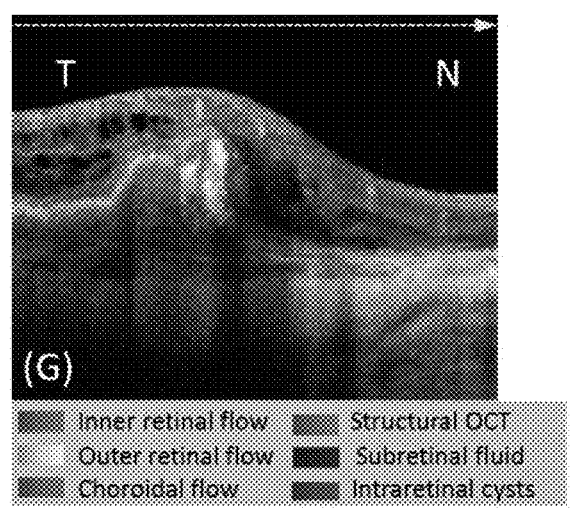

FIG. 14G is a cross-sectional color OCT angiogram showing the CNV both above and below the RPE. The subretinal hemorrhage was over the CNV and overshadowed the CNV at its nasal age.

Figure 14H:
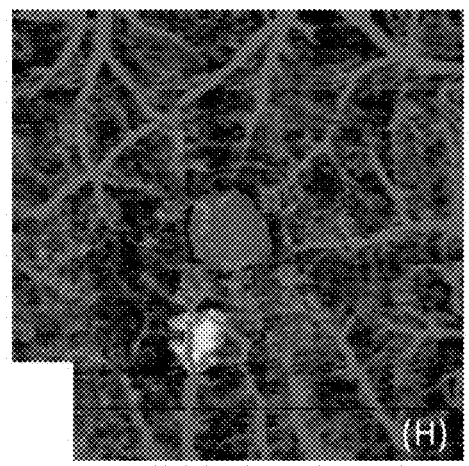

FIG. 14H is a composite en face OCT angiogram.

Figure 14I:
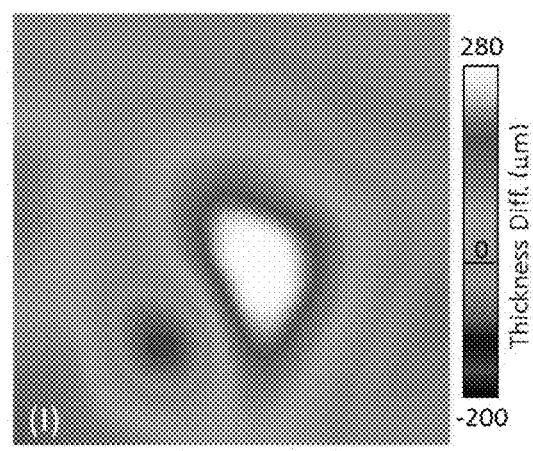

FIG. 14I is a retinal thickness deviation map showing thinning over the CNV and thickening around it.

Figure 15A:
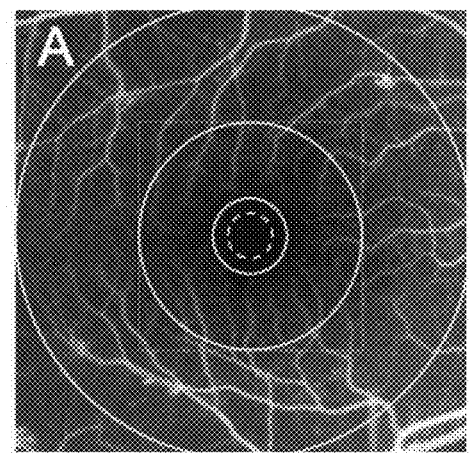

FIG. 15A is an image of the right eye of a subject with diabetic retinopathy showing fluorescein angiography cropped to 6×6 mm with an ETDRS grid superimposed.

Figure 15B:
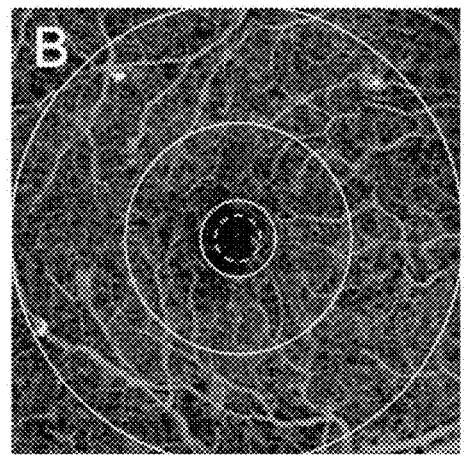

FIG. 15B is a 6×6 mm en face OCT retinal angiogram of the subject showing FAZ enlargement temporally between the 300 (dotted) and 500 μm diameter circles. The retinal flow signal, detected between Bruch's membrane and the internal limiting membrane is shown in magenta. Flow signal anterior to the ILM is shown in yellow, displaying small tufts of neovascularization.

Figure 15C:
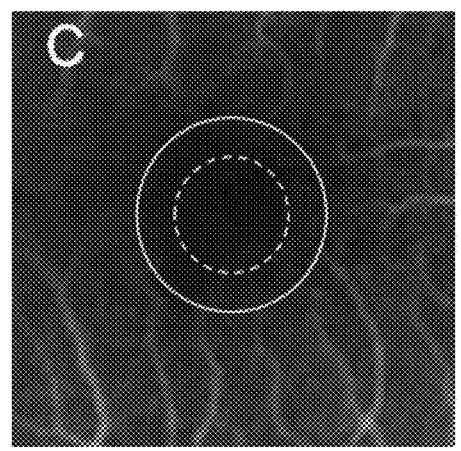

FIG. 15C is a magnified fluorescein angiography image of the subject showing the FAZ enlargement temporally.

Figure 16A:
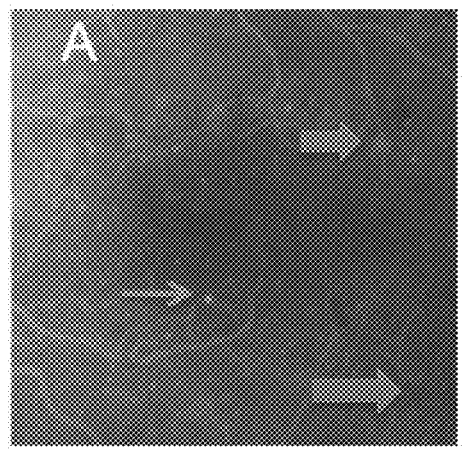

FIG. 16A is a 6×6 mm macular image of the left eye of a patient with proliferative diabetic retinopathy—in particular, an early frame fluorescein angiogram. Numerous microaneurysms are seen throughout the macula as punctate areas of hyperfluoresence. The green arrow points to an area of intraretinal microvascular abnormality (IRMA). The red arrow points to a small area of hyperfluoresence that leaked mildly in later frames.

Figure 16B:
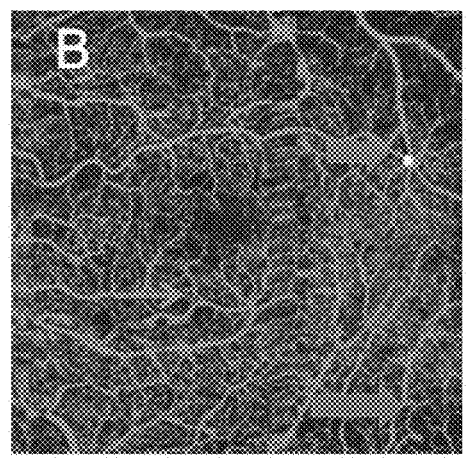

FIG. 16B is an en face OCT angiogram showing flow signal above the internal limiting membrane consistent with a tuft of neovascularization. The area of IRMA was also identified by OCT angiogram (green arrow). The largest microaneurysm on FA (blue arrow) was not identifiable on the OCT angiogram.

Figure 16C:
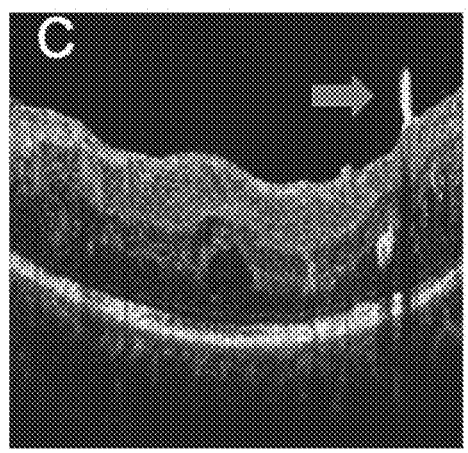

FIG. 16C is a cross-sectional OCT angiogram at the level of the neovascularization (yellow) shows it to be anterior to the ILM. Retinal circulation is colored in magenta and choroidal circulation (below Bruch's membrane is colored red.)

Figure 17A:
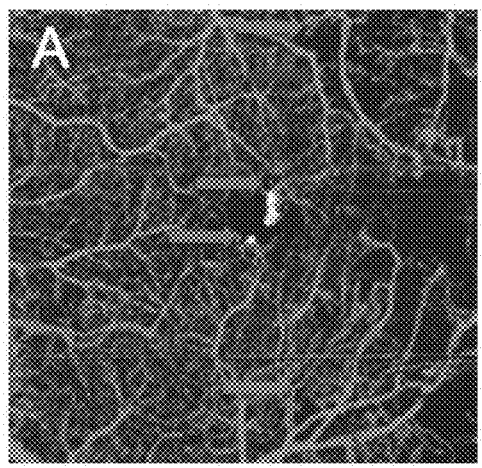

FIG. 17A is an OCT angiogram of a diabetic patient showing areas of capillary dropout in the temporal macula with pruning of the arterioles.

Figure 17B:
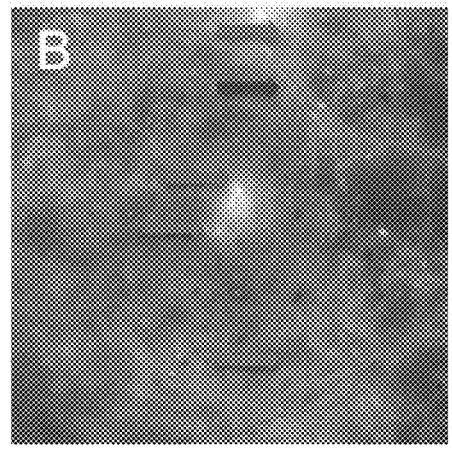

FIG. 17B is an image of fluorescent angiography of the same diabetic patient as in 17A showing areas of capillary dropout in the temporal macula with pruning of the arterioles. Diffuse leakage obscures an area of capillary drop out otherwise seen in the OCT. An arteriole with wall staining (blue arrow) in the FA is shown to be a barely visible ghost vessel in OCT. Focal areas of leakage near the fovea thought to be large microaneurysms in the FA were shown to be neovascularization by OCT.

Figure 17C:
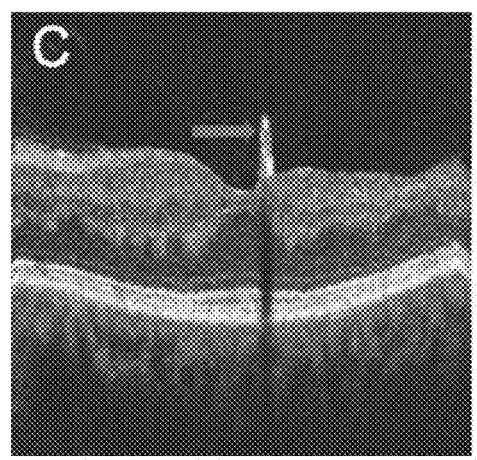

FIG. 17C is a cross-sectional OCT angiogram of the same diabetic patient as in FIGS. 17A and 17B.

Figure 18A:
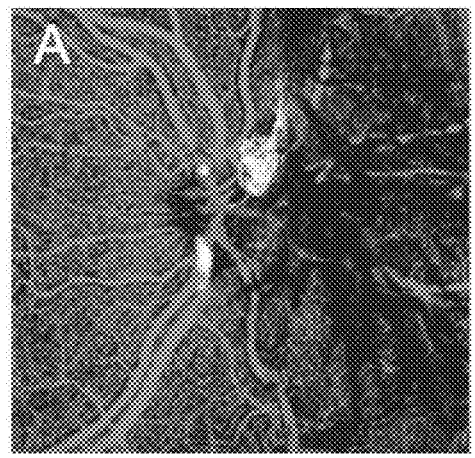

FIG. 18A is an en face OCT angiogram showing flow in the abnormal vessels above the disc. The NVD was cropped outside of the OCT scan volume nasal to the disc and is seen as shadows rather than flow.

Figure 18B:
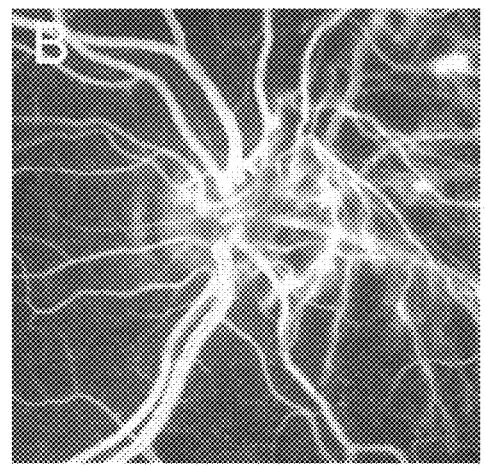

FIG. 18B shows that NVD is clearly seen using fluorescein angiography. Clinically, the NVD appeared elevated above the retinal surface.

FIGS. 19A-19F are images from OCT angiography (3×3 mm) of a healthy human eye acquired using a 70 kHz spectral OCT system with an 840 nm center wavelength.

Figure 19A:
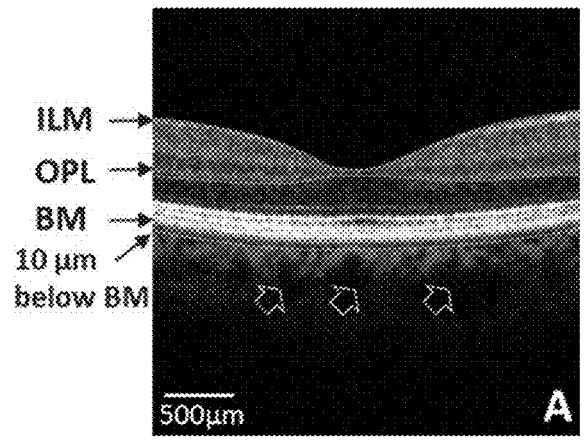

FIG. 19A is a Cross-sectional composite OCT angiogram. Depth layer segmentation lines are shown in green. ILM, internal limiting membrane; OPL, outer plexiform layer; BM, Bruch's membrane. Flow signals are color-coded by depth: purple, anterior to the OPL; red, posterior to BM.

Figure 19B:
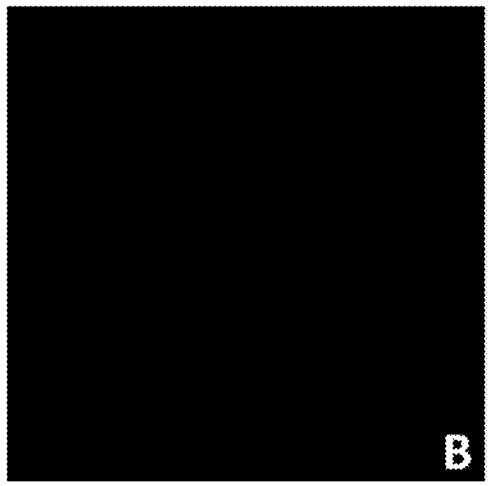

FIG. 19B is an en face OCT angiogram above the ILM shows the normal, avascular vitreous layer.

Figure 19C:
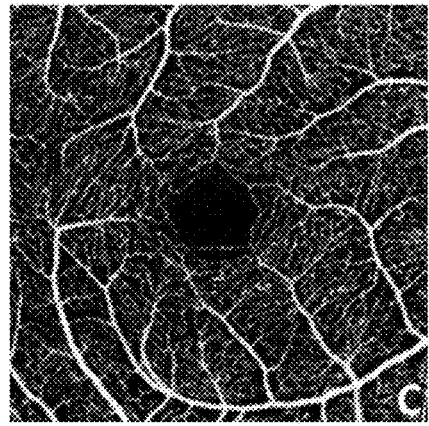

FIG. 19C is an en face OCT angiogram between the ILM and OPL that shows the normal retinal vasculature.

Figure 19D:
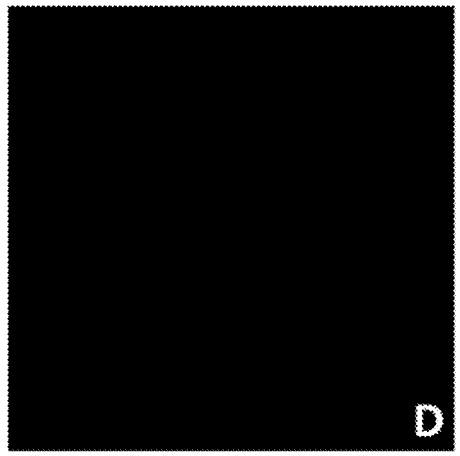

FIG. 19D is an en face OCT angiogram between the OPL and BM showing the normal, avascular outer retina.

Figure 19E:
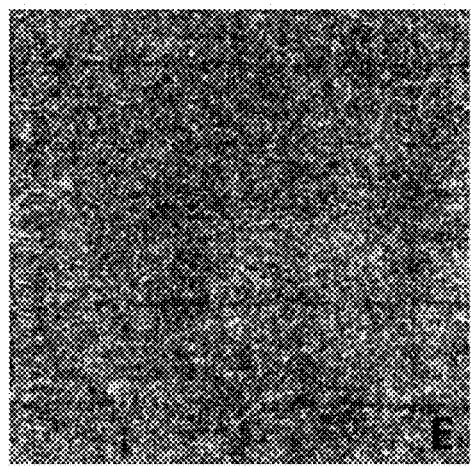

FIG. 19E is an en face OCT angiogram of the inner 10 μm of the choroid showing dense, relatively even flow throughout the central macula (3×3 mm).

Figure 19F:
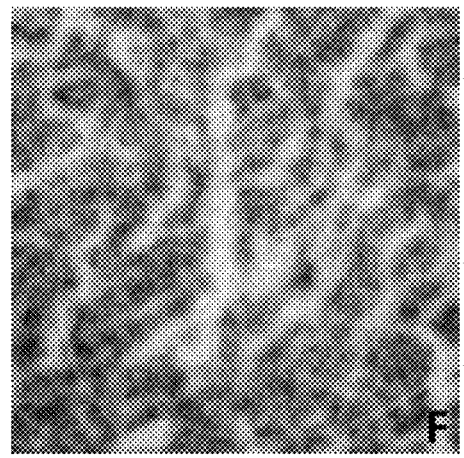

FIG. 19F is an en face OCT structural image with an inverse gray scale shows the deeper choroid with medium- and large-sized vessels.

FIGS. 20A-20D collectively are a quantification of inner retinal blood flows in a normal control subject (top panels of 20A-20D) and in a subject with non-proliferative diabetic neuropathy with macular edema (bottom panels of 20A-20D). OCT angiography was acquired using a 70 kHz spectral OCT system with a center wavelength of 840 nm. The white dashed circle represents the normal foveal avascular zone (FAZ, 0.6 mm diameter white dashed circle). The area between the white and blue dashed circles is the parafoveal zone. The area between blue and green dashed circles is the perifoveal zone. The normal subject had a FAZ of 0.30 mm$^2$, while the NPDR case showed an enlarged FAZ and scattered areas of macular non perfusion totaling 7.07 mm$^2$.

Figure 20A:
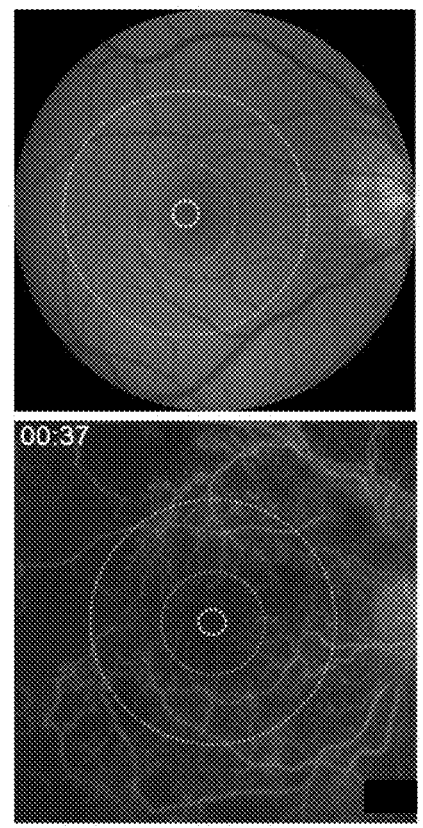

FIG. 20A (top panel) is a fundus photo of the normal control subject.

FIG. 20A (bottom panel) is a fluorescein angiogram of a subject with non-proliferative diabetic neuropathy.

Figure 20B:
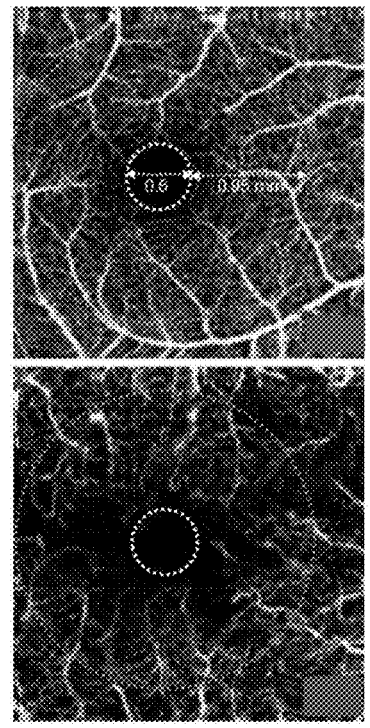

FIG. 20B (top panel) is an en face 3×3 mm OCT angiogram of normal control subject.

FIG. 20B (bottom panel) is an en face 3×3 mm OCT angiogram of a subject with non-proliferative diabetic neuropathy. Enlargement of the FAZ is present in the parafoveal region.

Figure 20C:
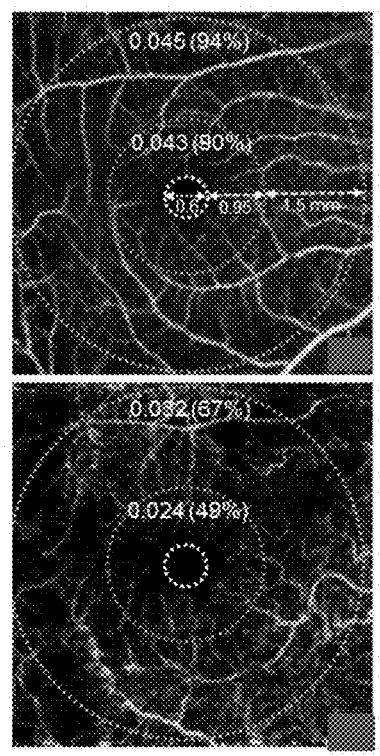

FIG. 20C (top panel) is a parafoveal and perifoveal retinal flow index (vessel density) shown on am en face 6×6 mm OCT angiogram in a normal control subject.

FIG. 20C (bottom panel) is a parafoveal and perifoveal retinal flow index (vessel density) shown on am en face 6×6 mm OCT angiogram in a subject with non-proliferative diabetic neuropathy.

Figure 20D:
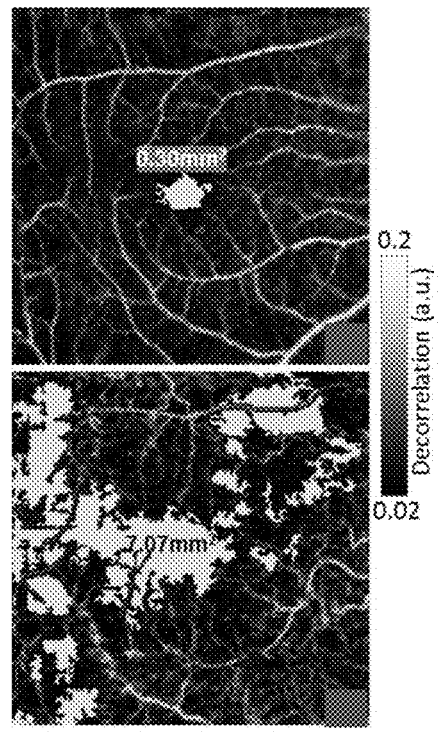

FIG. 20D (top panel) is an angiogram showing nonperfusion areas (blue) in a normal control subject.

FIG. 20D (bottom panel) is an angiogram showing non-perfusion areas (blue) in a a subject with non-proliferative diabetic neuropathy.

FIG. 21A-D collectively show a proliferative diabetic retinopathy (PDR) case imaged using a 100 kHz swept-source OCT system with a center wavelength of 1050 nm.

Figure 21A:
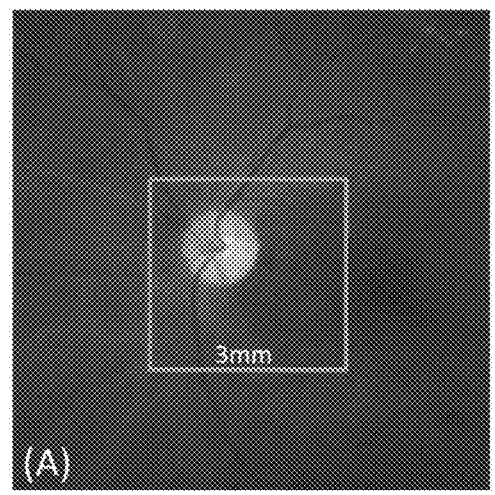

FIG. 21A is a confocal scanning laser ophthalmoscope (cSLO) showing retinal neovascularization (NVD) at the optic disc and attenuated retinal vessels.

Figure 21B:
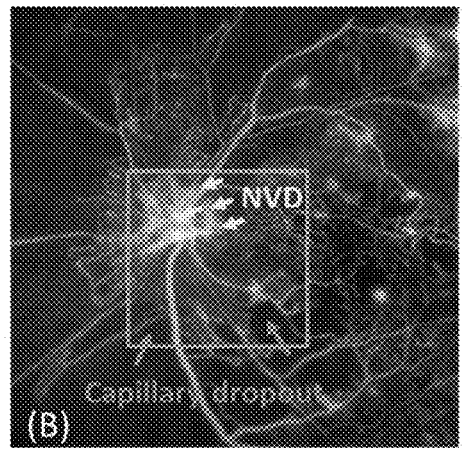

FIG. 21B is an FA image showing NVD and peripapillary capillary dropout. The green squares in A and B outline the 3×3 mm area shown on the OCT angiogram below.

Figure 21C:
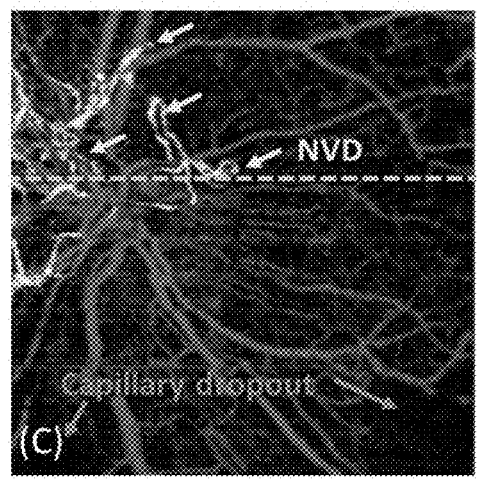

FIG. 21C is an en face OCT angiography showing NVD and areas of capillary dropout that correspond to FA (NV is shown in light red gold; normal retinal vessels in purple). The area of NVD was 0.47 mm$^2$. The vitreous flow index was 0.022.

Figure 21D:
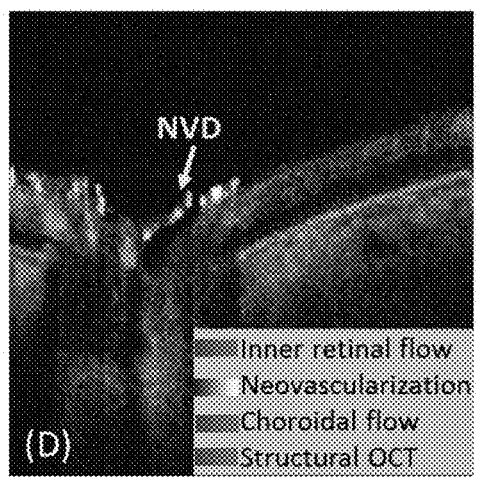

FIG. 21D is a Cross-sectional composite OCT angiogram showing NVD above the inner limiting membrane (red gold).

FIGS. 22A-22D collectively show a type I CNV case imaged by a 100 kHz swept-source OCT system with a center wavelength of 1050 nm. The CNV is identified by OCT angiography (3×3 mm), but it is ill-defined by fluorescein angiography (FA).

Figure 22A:
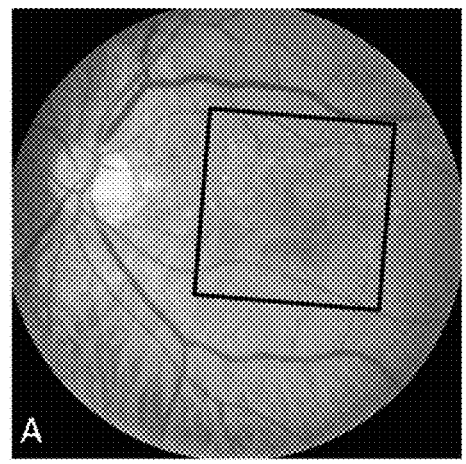

FIG. 22A is a fundus photograph. The black square outlines the areas shown on the angiograms.

Figure 22B:
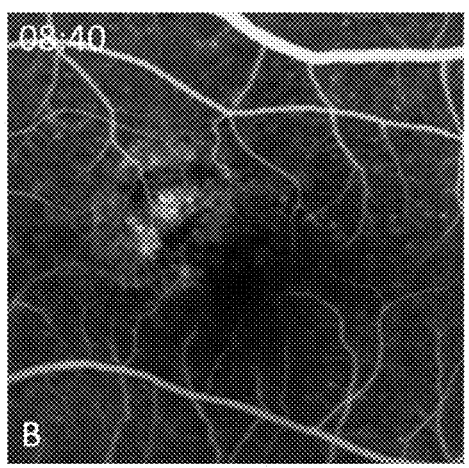

FIG. 22B is a late stage fluorescein angiograph showing an occult CNV.

Figure 22C:
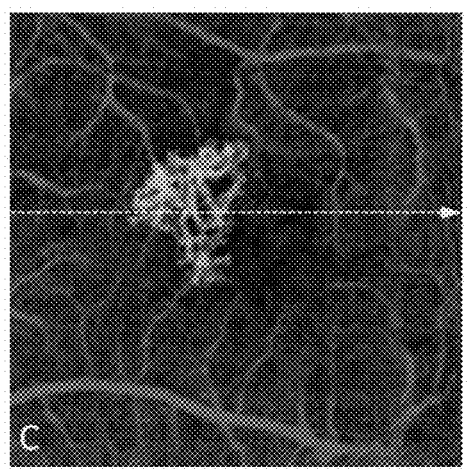

FIG. 22C is a composite en face color-coded OCT angiogram with CNV flow highlighted in yellow. The CNV area was 0.96 mm$^2$ and the outer retina flow index was 0.012. The yellow dashed line indicates the position of the OCT cross-section.

Figure 22D:
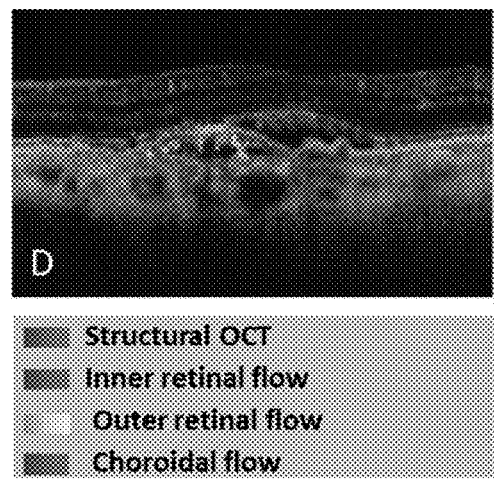

FIG. 22D is a cross-sectional color OCT angiogram.

Both composite en face (C) and cross-sectional color OCT angiograms (D) show inner retinal flow in purple, outer retinal flow (CNV) in yellow, and choroidal flow in red. The CNV is predominantly under the RPE.

FIGS. 23A-23F collectively show a geographic atrophy case imaged by a 100 kHz swept-source OCT system with a center wavelength of 1050 nm.

Figure 23A:
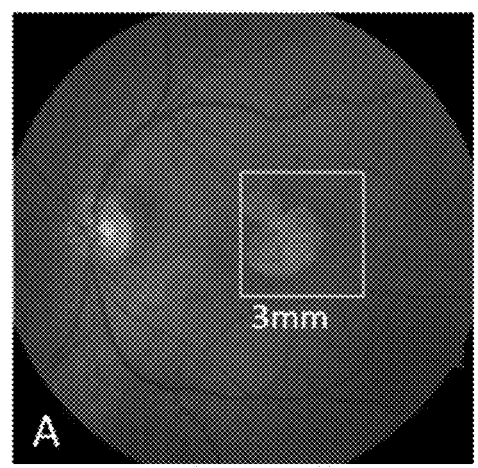

FIG. 23A is a fundus photograph showing the area of geographic atrophy (GA) adjacent to the foveal center.

Figure 23B:
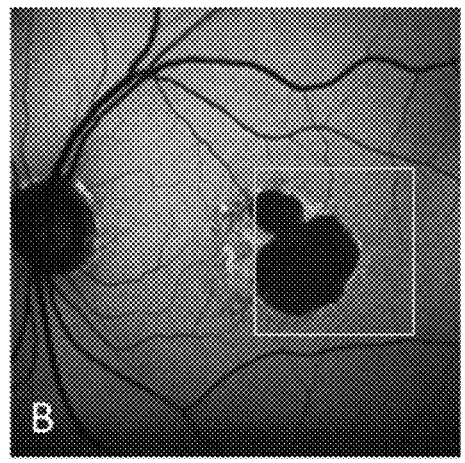

FIG. 23B is an autofluorescence image sharply outlines the area of absent RPE and is surrounded by a halo of hyperautofluorescence. The green squares in FIGS. 23A and 23B outline the area shown in FIGS. 23C-F.

Figure 23C:
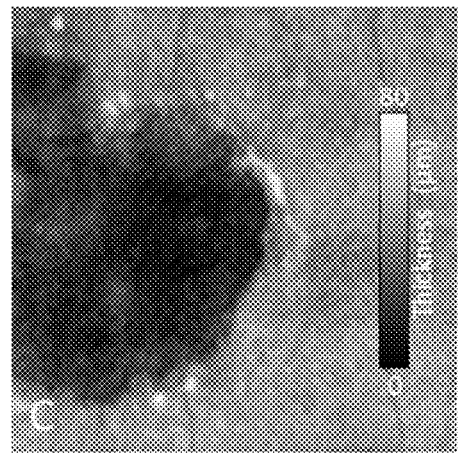

FIG. 23C is a drusen-RPE complex thickness map showing the area of RPE thinning (the dark area nasally)

Figure 23D:
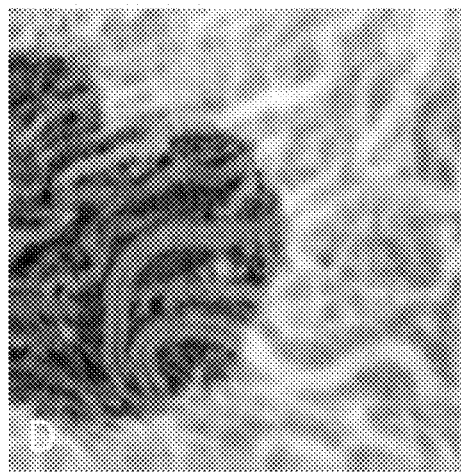

FIG. 23D is an en face OCT structural image on an inverse gray scale of the deeper choroid reveals medium- and large-sized vessels.

Figure 23E:
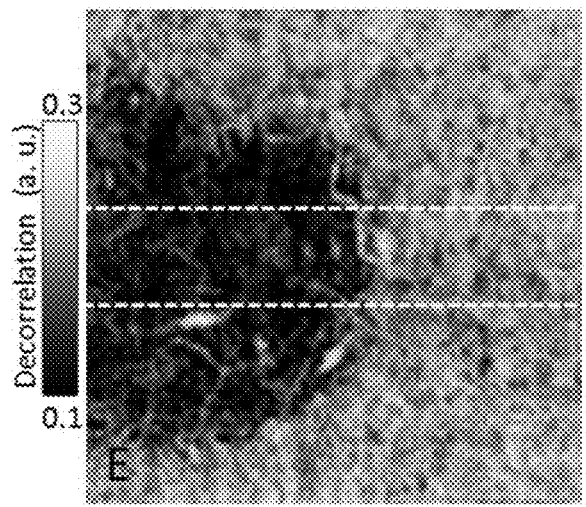

FIG. 23E is an en face OCT angiogram (3×3 mm) of the choriocapillaris showing dramatically decreased, but not absent, choriocapillaris flow in the area of GA.

Figure 23F:
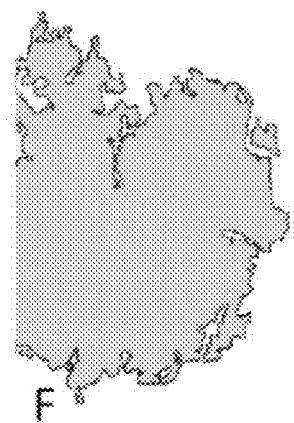

FIG. 23F is a map of the same en face OCT angiogram of FIG. 23E. The light blue color represents the choriocapillaris nonperfusion area (2.75 mm$^2$).

Figure 23G:
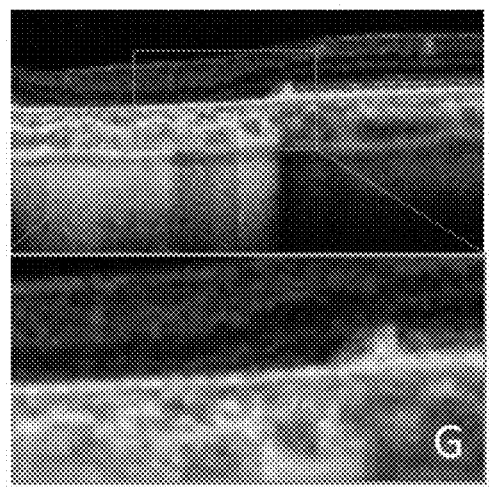
Figure 23H:
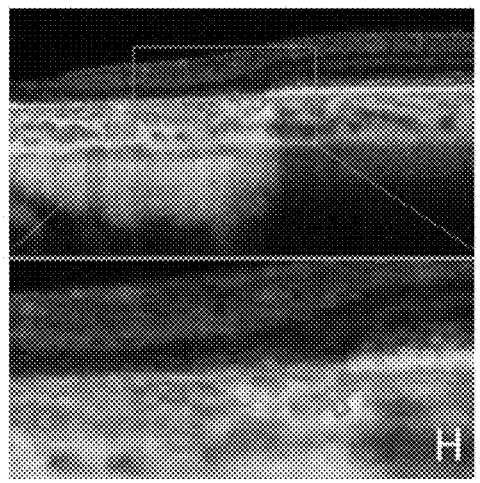

FIG. 23G is a cross-sectional composite OCT angiogram showing the absence of choriocapillaris flow in most of the area of GA, FIG. 23H is a cross-sectional composite OCT angiogram showing that flow at the edge of the atrophy is spared (shown by the green arrows in the magnified views).

FIGS. 24A-24E collectively show a choroideremia case imaged by a 100 kHz swept-source OCT system with a center wavelength of 1050 nm. The large-field en face OCT angiograms (~3×8.5 mm) were produced by stitching together three 3×3 mm scans.

Figure 24A:
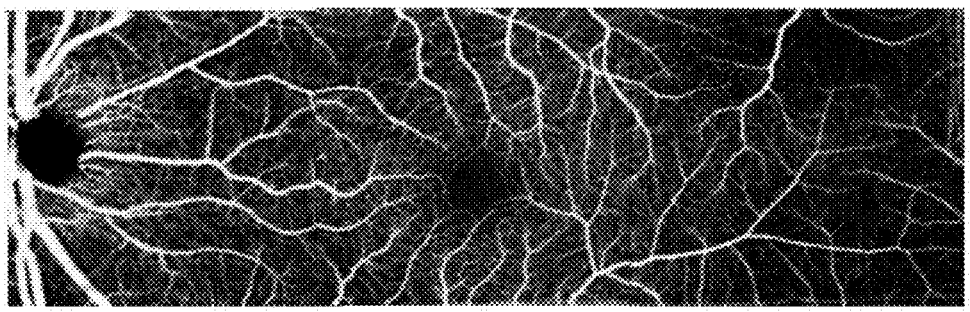

FIG. 24A is an image resulting from OCT angiography of inner retinal blood flow.

Figure 24B:
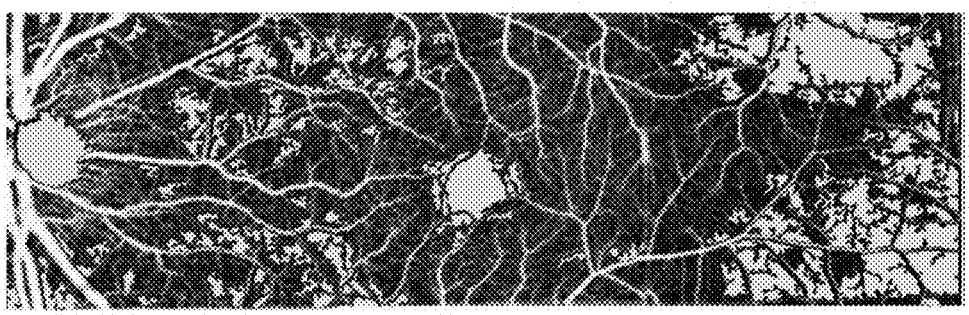

FIG. 24B is an image resulting from OCT angiography with quantification of inner retinal blood flow demonstrating patchy areas of nonperfusion (blue) in the extra-foveal macula. The total nonperfusion area of the inner retina was 7.65 mm$^2$.

Figure 24C:
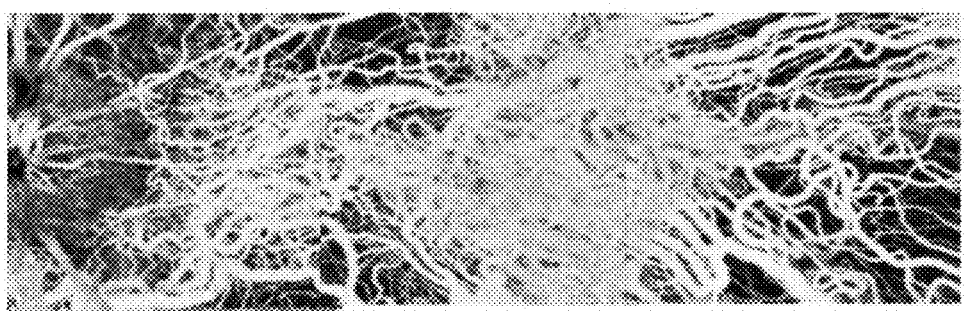

FIG. 24C is an image resulting from OCT angiography of the choroidal blood flow, including choriocapillaris and deep choroid. It should be noted that OCT angiography is able to image deeper choroidal vessels in this case due to the relative absence of the overlying choriocapillaris and RPE.

Figure 24D:
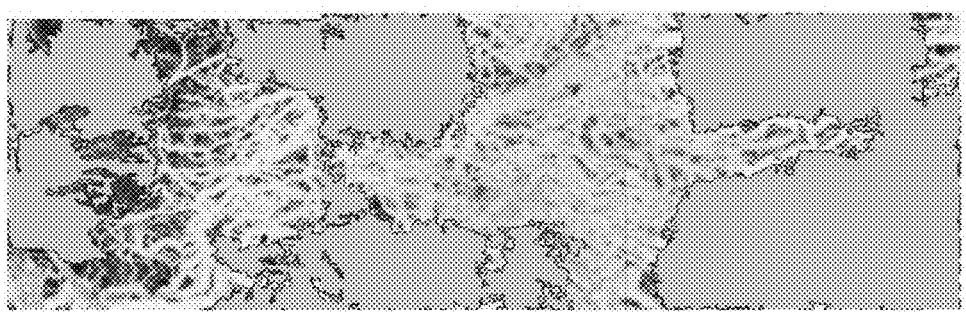

FIG. 24D is an image resulting from OCT angiography of the choroidal blood flow with quantification of the choriocapillaris nonperfusion area (purple), which was 12.11 mm$^2$ (47.5% of image area).

Figure 24E:
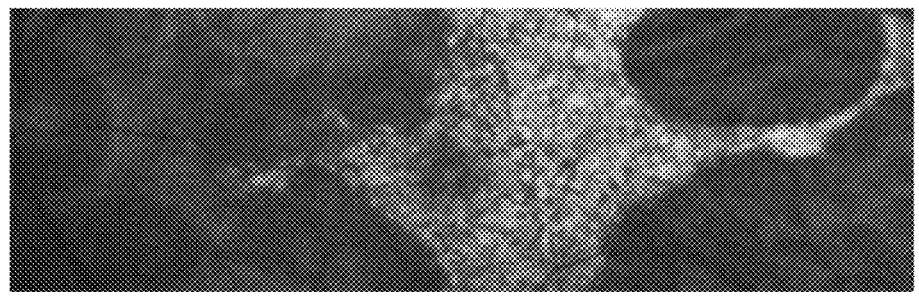

FIG. 24E is an autofluorescence image outlined the area of existing RPE (hyperautofluorescent area).

Figure 25:
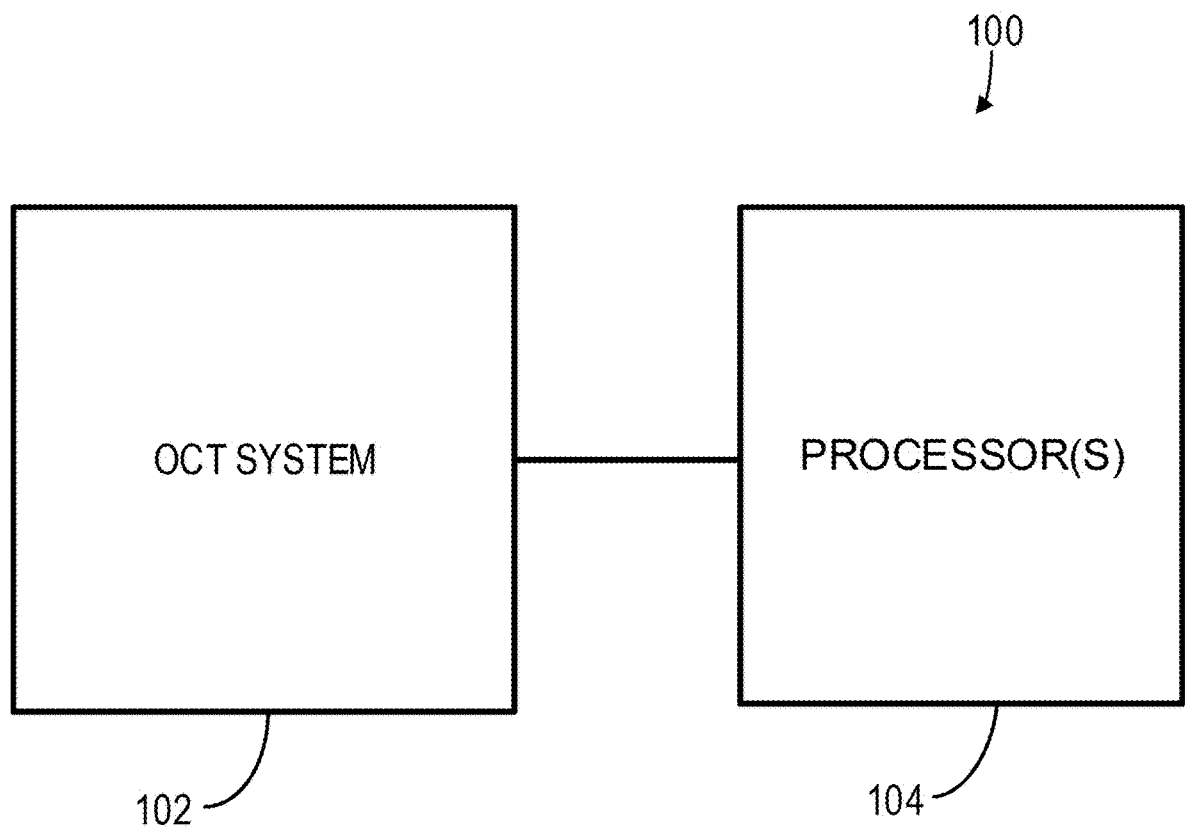

FIG. 25 is a schematic of a system for processing OCT angiography data in accordance with the disclosure.

Figure 26:
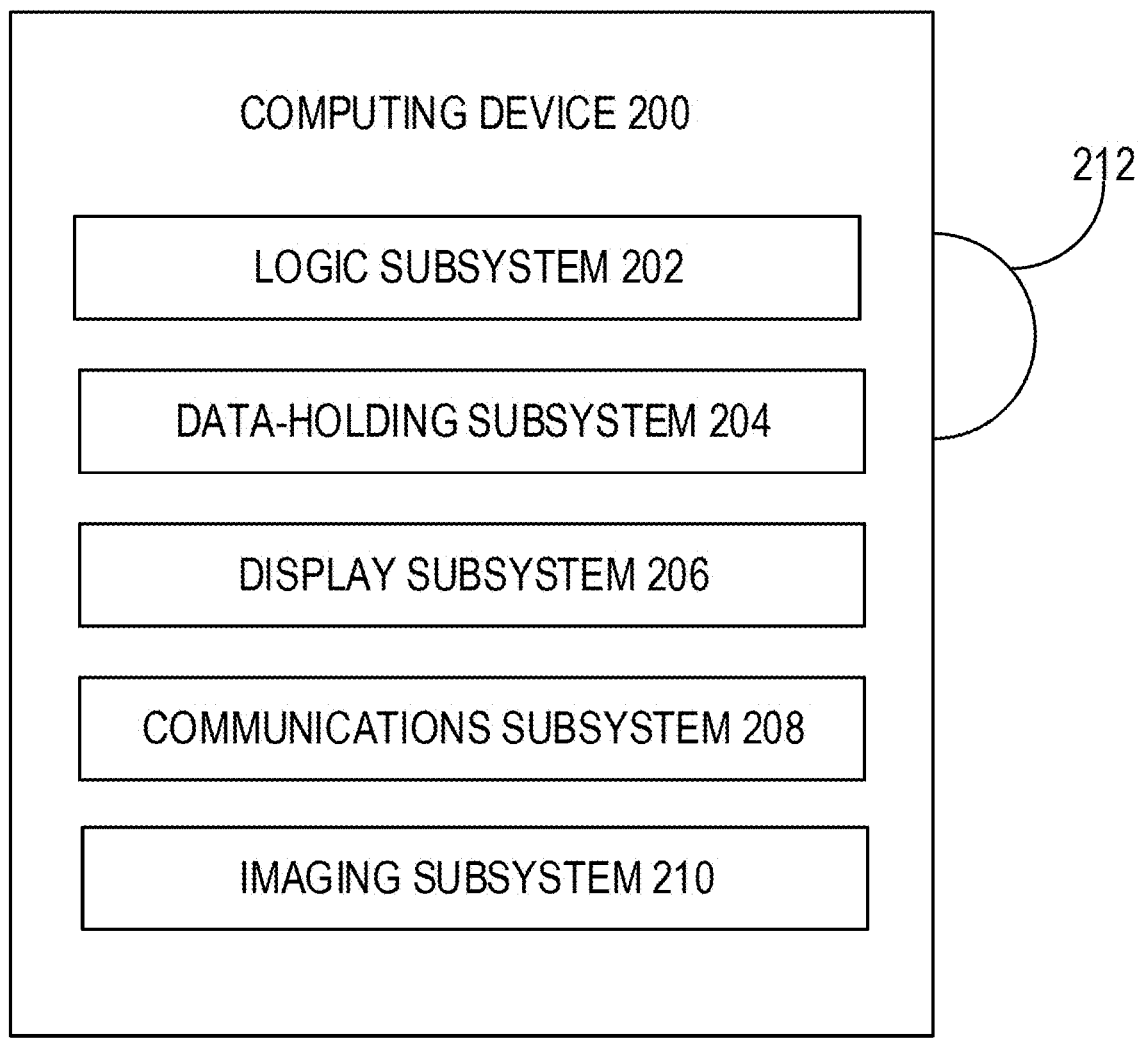

FIG. 26 is an example of a computing system in accordance with the disclosure.

DETAILED DESCRIPTION

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, structure and/or flow information of a sample can be obtained using OCT (structure) and OCT angiography (flow) imaging-based on the detection of spectral interference. Such imaging can be two-dimensional (2-D) or three-dimensional (3-D), depending on the application. Structural imaging can be of an extended depth and scan-width range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures within an item of interest. An A-scan is an axial scan directed along the optical axis of the OCT device and penetrates the sample being imaged. The A-scan encodes reflectivity information (for example, signal intensity) as a function of depth.

B-scan: A cross-sectional tomograph that can be achieved by laterally combining a series of axial depth scans (i.e., A-scans) in the x-direction or y-direction. A B-scan encodes planar cross-sectional information from the sample and is typically presented as an image. Thus, a B-scan can be called a cross sectional image.

C-scan: A cross-sectional tomograph that can be achieved by combining a series of voxels at a given axial depth (i.e., z-direction) in a 3D OCT dataset. A C-scan encodes planar cross-sectional information from the sample and is typically presented as an image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value or a decorrelation value). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A C-scan is made up of voxels at a specified depth (z-axis) in the data set; a B-scan can also be referred to as an image, and its constituent voxels referred to as pixels. A collection of adjacent B-scans or a collection of adjacent C-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset of decorrelation values reflecting flow within the imaged sample. There is a one-to-one correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a projection of the three dimensional dataset onto a single planar image called an en face angiogram (Wallis J et al, *Med Imaging IEEE Trans* 8, 297-230 (1989); Wang R K et al, 2007 supra; Jia Y et al, 2012 supra; incorporated by reference herein). Construction of such an en face angiogram requires the specification of the upper and lower depth extents that enclose the region of interest within the retina to be projected onto the angiogram image. These upper and lower depth extents can be specified as the boundaries between different layers of the retina (e.g., the voxels between the inner limiting membrane and outer plexiform layer can be used to generate a 2D en face angiogram of the inner retina). Once generated, the en face angiogram image may be used to quantify various features of the retinal vasculature as described herein. This quantification typically involves the setting of a threshold value to differentiate, for example, the pixels that represent active vasculature from static tissue within the angiogram. These 2D en face angiograms can be interpreted in a manner similar to traditional angiography techniques such as fluorescein angiography (FA) or indocyanine green (ICG) angiography, and are thus well-suited for clinical use.

System

A high-speed swept-source OCT system at 1050 nm wavelength provides for deeper penetration compared with standard 830 nm OCT and thus results in improved imaging below the RPE. An OCT system configured to perform OCT angiography can further be used to detect blood flow within retina as well as above and below it. For example, an OCT angiography system using the spit-spectrum amplitude decorrelation algorithm (SSADA) can be used to process data from the OCT system. SSADA is based on detecting the reflectance amplitude (or intensity) variation over time due to flow in vascular volumes. Neither amplitude- nor intensity-based OCT angiography requires accurate determination of background tissue phase variation due to motion, and are therefore more robust than Doppler or phase-based OCT angiography approaches (Tokayer J et al, *Biomed Opt Express* 4, 1909-1924 (2013) and US Patent Application Number 20120307014, both of which are incorporated by reference herein). The SSADA algorithm improves on the standard amplitude or intensity-based algorithms (Hendargo H C et al, *Biomed Opt Express* 4, 803-821 (2013); Mariampillai A et al, *Opt Lett* 33, 1530-1532 (2008); Enfield J et al, *Biomed Opt Express* 2, 1184-1193 (2011); and Motaghiannezam R and Fraser S, *Biomed Opt Express* 3, 503-521 (2012); all of which are incorporated by reference herein) by enhancing signal and suppressing noise through spectral splitting of the OCT images (Ferris F L et al, *Arch Ophthalmol* 102, 1640-1642 (1984); incorporated by reference herein).

The system further involves methods for segmenting 3D angiograms into separate vascular layers, for example, the inner retina, the outer retina, and the choroid. Because the outer retinal layer is normally devoid of blood flow, it is possible, for instance, to provide a clean en face visualization of the any CNV structure invading the outer retinal space using the system. The method further involves optimizing the choice of color and transparency used to display blood flow associated with specific retinal layers, which grants the ability to highlight the pathologic features such as neovascularization relative to the other layers in a composite en face angiogram.

Other evidence of vascular pathology, such as subretinal fluid and intraretinal cysts, can also be incorporated into the composite view. This may be helpful to the clinician in the rapid assessment of retinal vascular disease and its response to treatment. Because both functional (blood flow) and structural (fluid accumulations) information are taken from a single OCT scan, they are naturally perfectly registered. This provides the advantages of being simpler as well as potentially faster and more robust than combining structural OCT with FA or ICG angiography taken from separate instruments.

Disclosed herein are methods of using OCT angiography, to identify ocular pathologies by the abnormal presence of flow in layers that usually lack blood vessels or the absence of flow in normally vascular layers. The depth-revolved nature of OCT angiography, both in 2D and 3D implementations, allows separate evaluation of abnormalities in retinal and choroidal circulations. Because dye leakage and staining associated with FA and ICG angiography do not occur in OCT angiography, the boundaries, and therefore areas, of capillary dropout and neovascularization can be measured using the disclosed methods. Thus, quantitative information, such as vessel density, vessel area, and non-perfusion area, can be obtained. The disclosed methods may be used with any OCT system capable of providing structural and OCT angiography data, but systems with suitably high scan speeds and depth may be advantageous in clinical use. For instance, OCT angiography systems using the SSADA algorithm (Jia Y et al, (2012) supra) can acquire clinically useful data in a few seconds, a dramatic improvement compared to several minutes for FA., Furthermore, the scan pattern and SSADA processing can be implemented on spectral-domain or swept-source OCT systems without any special hardware modification provided that imaging speeds are sufficient, i.e. ≥70 kHz is required to provide 6×6 mm angiograms with capillary details within a reasonable scan time (≤3 sec).

Applications

Figure 1:
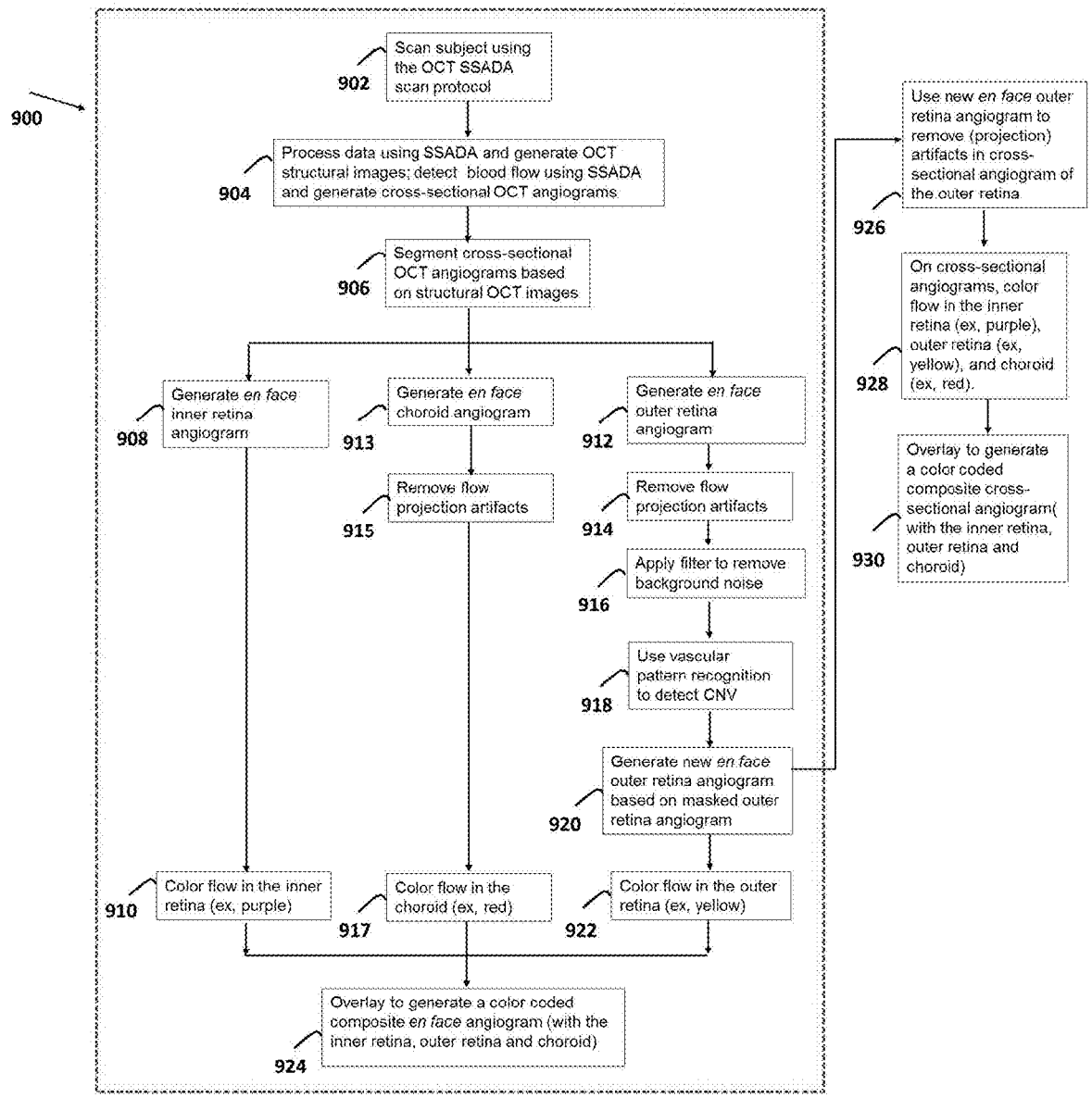
FIG. 1 is a flow chart of an example of a method of generating an en face color coded composite angiogram.

Computer based methods of using optical coherence tomography (OCT) angiography are disclosed. One example of such a method 900 is outlined in FIG. 1 herein. The method in FIG. 1 is a computer based method used to generate a color coded composite en face angiogram and a color coded composite cross-sectional angiogram showing the inner retina, outer retina and choroid. The subject's eye is scanned using an OCT scan protocol 902. The data are processed using, for example the SSADA algorithm 904 thereby generating a set of cross-sectional OCT structural images and an en face structural OCT image. Each cross-sectional OCT structural image is segmented into a cross-sectional inner retina OCT structural image, a cross-sectional outer retina OCT structural image and a cross-sectional choroid OCT structural image. The segmentation can be performed automatically by the software or by the end user using a graphical user interface or other input device. Blood flow is also detected, for example, using the SSADA algorithm 904 thereby generating a set of cross-sectional OCT angiograms. Following the segmentation of the corresponding cross-sectional OCT structural image, each cross-sectional OCT angiogram is then segmented 906 into a cross-sectional inner retina angiogram, a first cross-sectional outer retina angiogram and a cross-sectional choroid angiogram. An en face inner retina angiogram visualizes retinal vasculature. The en face inner retina angiogram is generated by projecting the cross-sectional inner retina angiograms 908. A first en face outer retina angiogram is generated by projecting the (first) cross-sectional outer retina angiograms 912. The inner retina is defined as the area between the inner limiting membrane (ILM) and the outer boundary of the outer plexiform layer (OPL). The outer retina is defined as being between the outer boundary of the outer plexiform layer and Bruch's membrane (BM). Blood flow in the inner retina angiogram is assigned a first color 910. Flow projection artifacts resulting from the projections of inner retinal flow are removed from the en face outer retina angiogram 914. A filter, such as a Gaussian filter or a low pass filter is used to remove additional background noise 916. Choroidal neovascularization (CNV) is detected using pattern recognition 918. Examples of pattern recognition approaches include saliency based approaches that use features such as gradient, direction, and brightness to recognize CNV. When the CNV is detected, a second en face outer retina angiogram that shows the CNV is produced 920. Blood flow in the outer retinal angiogram is assigned a second color 922. An en face choroid angiogram is generated by projecting the cross-sectional choroid angiograms 913. Flow projection artifacts resulting from the projections of inner retinal flow are removed from the en face choroid angiogram 915. Blood flow in the choroid angiogram is assigned a third color 917. A color coded composite en face angiogram with inner retina, outer retina and choroid is generated 924 from overlaying the en face inner retina angiogram, the second en face outer retina angiogram and the en face choroid angiogram upon the en face structural OCT image. The information in the second en face outer retina angiogram is used to remove projection artifacts on the first cross-sectional outer retina angiogram 926. A second cross-sectional outer retina angiogram that shows the CNV is produced 928. Blood flow in the inner retina, outer retina, choroid angiogram are assigned a first, second, third color respectively 928. A color coded composite cross-sectional angiogram with inner retina, outer retina and choroid 930 is generated from overlaying the cross-sectional inner retina angiogram, the second cross-sectional outer retina angiogram and the cross-sectional choroid angiogram upon the corresponding structural OCT cross-sectional image.

Figure 2:
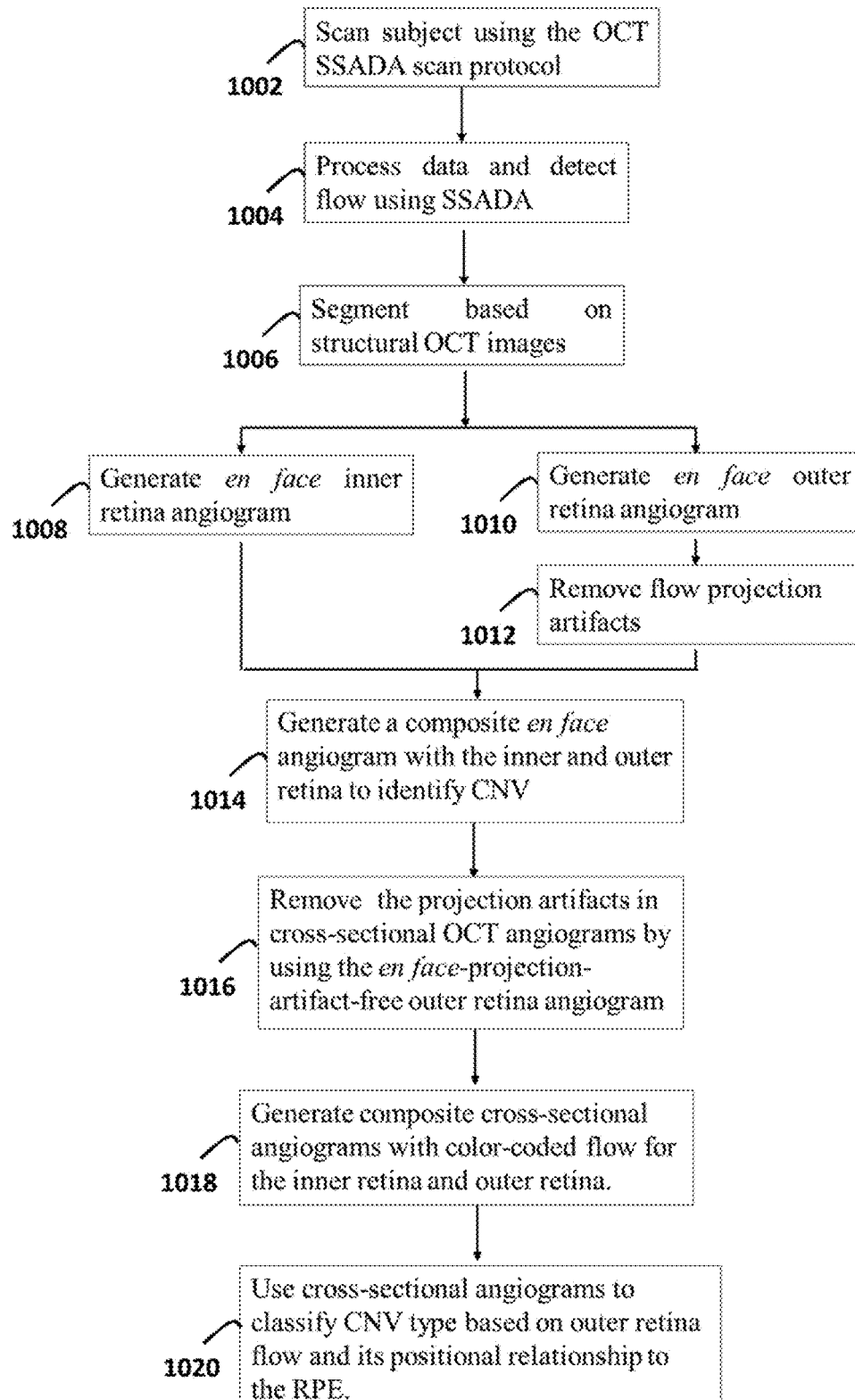
FIG. 2 is a flow chart of an example of a method of visualizing choroidal neovascularization.

A second example is a method of using OCT to visualize choroidal neovascularization (CNV) 1000 as outlined in FIG. 2 herein. In this method, a subject is scanned using an OCT scan protocol such as SSADA 1002. The data is processed using, for example, the SSADA algorithm 1004 thereby generating a set of cross-sectional OCT structural images and an en face structural OCT image. Each cross-sectional OCT structural image is segmented into a cross-sectional inner retina OCT structural image and a cross-sectional outer retina OCT structural image. The segmentation can be performed automatically by the software or by the end user using a graphical user interface or other input device as described above. Blood flow is detected using, for example, the SSADA algorithm 1004 thereby generating a set of cross-sectional OCT angiograms as described above. Following the segmentation of the corresponding cross-sectional OCT structural image, each cross-sectional OCT angiogram is then segmented 1006 into a cross-sectional inner retina angiogram and a first cross-sectional outer retina angiogram. An en face inner retina angiogram is generated by projecting the cross-sectional inner retina angiograms 1008 and a first en face outer retina angiogram is generated by projecting the first cross-sectional outer retina angiograms 1010. Flow projection artifacts are removed from the first en face outer retina angiogram as described above 1012, thereby generating a second en face outer retina angiogram. A composite en face angiogram with inner and outer retina is generated 1014 from overlaying the en face inner retina angiogram and the second en face outer retina angiogram. The blood flow in the composite en face angiogram can be color coded 1014. In the composite angiogram, flow detected in the outer retina is an indication of CNV 1014. The information in the second en face outer retina angiogram can be used to remove projection artifacts in the first cross-sectional outer retina angiogram 1016, thereby generating a second cross-sectional outer retina angiogram. A composite cross-sectional angiogram 1018 is then generated from overlaying the cross-sectional inner retina angiogram and the second cross-sectional outer retina angiogram on the corresponding cross-sectional OCT structural image. The blood flow in the composite cross-sectional angiogram can be color coded. The color coded cross-sectional angiogram can then be used to classify the CNV type 1020. CNV type can be classified based on the blood flow relative to the retinal pigment epithelium (RPE). Type I CNV occurs between the RPE and BM, Type II occurs above the RPE, and Type III occurs in the inner retina. Combined types occur in any combination thereof.

Figure 3:
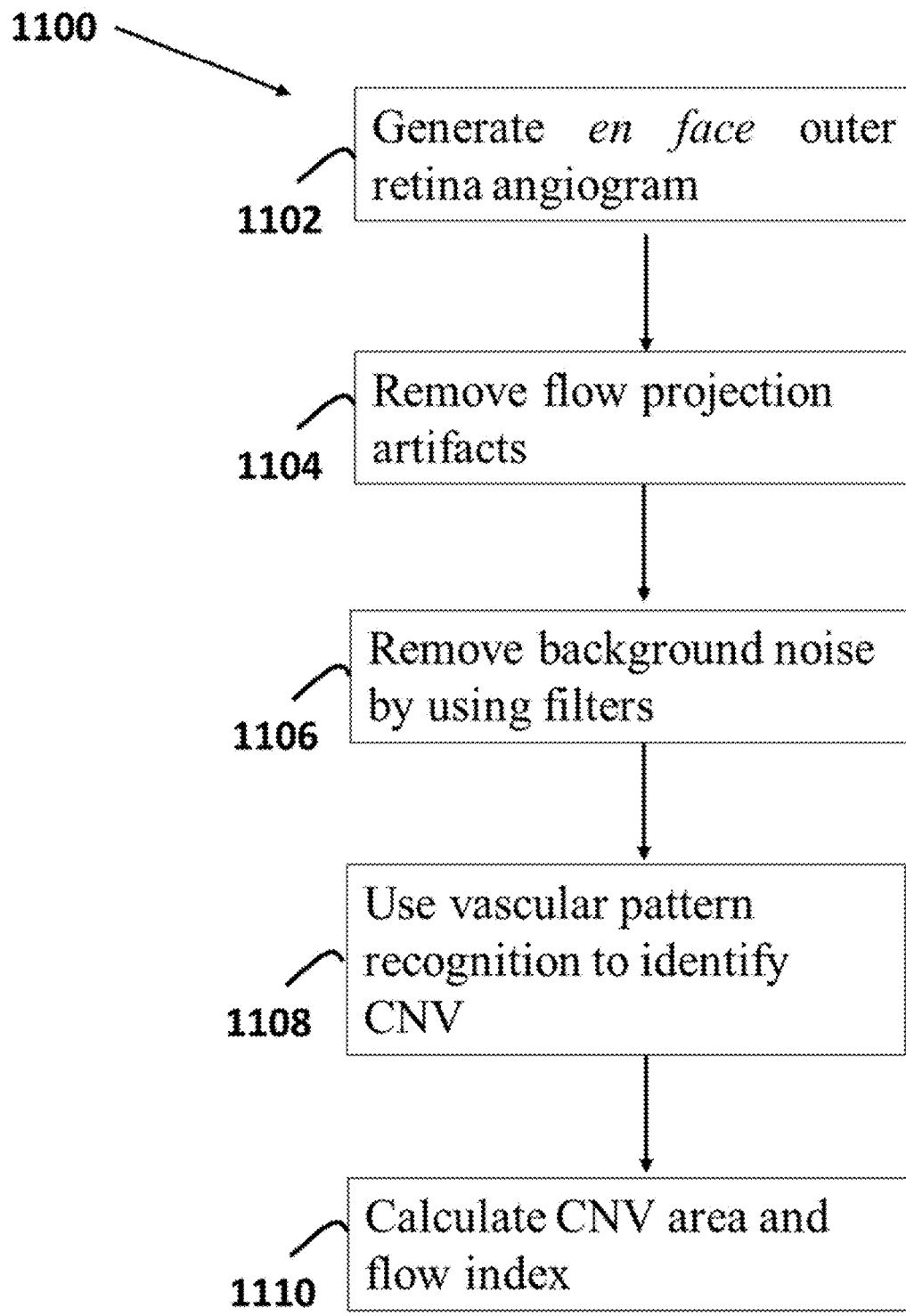
FIG. 3 is a flow chart of an example of a method of measuring choroidal neovascularization area and flow index area.

A third example is a method of using OCT to measure the area of the choroidal neovascularization (CNV) and flow index 1100 as outlined in FIG. 3 herein. An en face outer retina OCT angiogram is generated as described above 1102. Flow projection artifacts are removed as described above 1104. Background noise is removed using filters as described above 1106. Vascular pattern recognition is used to identify CNV as described above 1108 and the CNV area and flow index are determined 1110. CNV area can be determined by summing the number of pixels for which the decorrelation value is above that of the background and converting the sum to physical dimensions (for example, $mm^2$). CNV flow index can be determined by summing the decorrelation value of the pixels that encompass the CNV and then dividing by the area of the en face outer retina angiogram.

Figure 4:
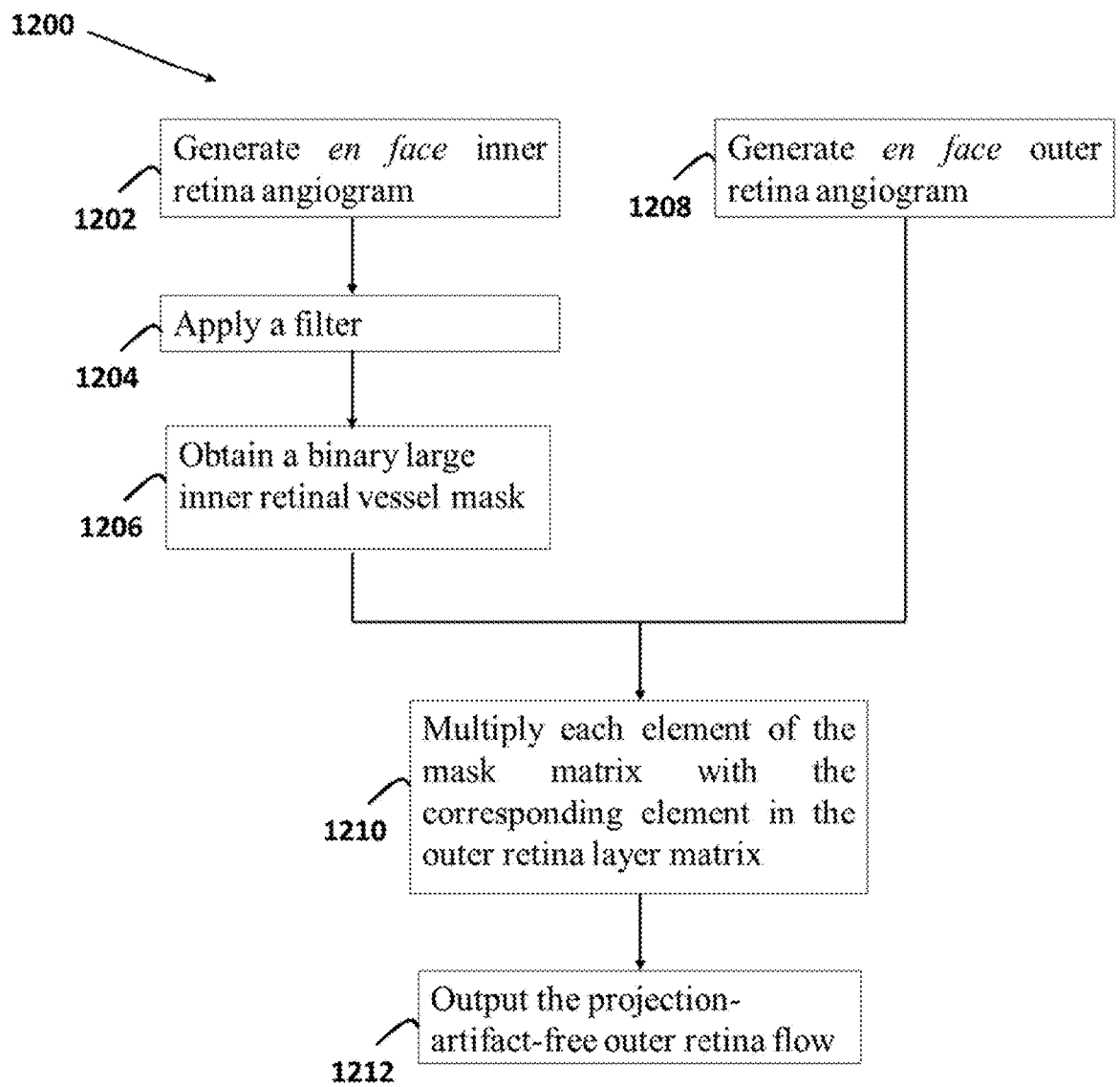
FIG. 4 is a flow chart of an example of a method of removing projection artifacts in an OCT angiogram of the outer retina.

A fourth example is a method of removing projection artifacts in an OCT angiogram of the outer retina 1200 as outlined in FIG. 4 herein. This example involves generating an en face inner retina angiogram 1202, applying a filter (such as a Gaussian or low pass filter) to the en face inner retina angiogram. The filter removes small internal retinal vessels from the image 1204. Application of the filter results in a binary large inner retinal vessel mask 1206. The example further involves generating an en face outer retina angiogram 1208 and removing projection artifacts in the en face outer retina OCT angiogram by multiplying each element of the mask matrix with the corresponding element in the outer retina layer matrix 1210. The result can be output as a matrix presenting artifact-free en-face outer retina flow or an artifact-free en-face outer retina flow angiogram 1212. The information in the artifact-free en-face outer retina angiogram can be used to remove projection artifacts in the cross-sectional outer retina angiogram 1214, thereby generating an artifact-free cross-sectional outer retina flow angiogram 1216.

Figure 5:
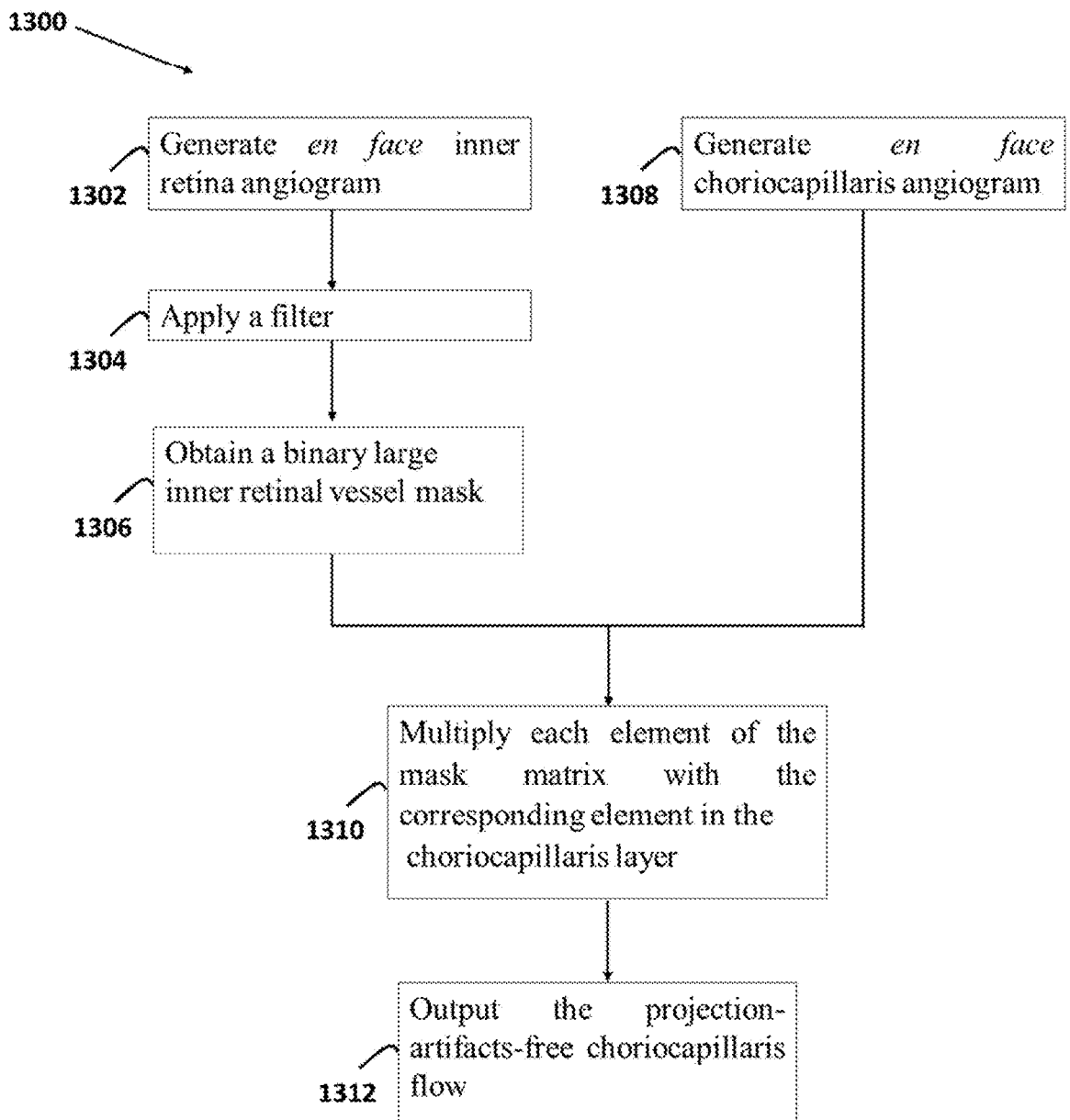
FIG. 5 is a flow chart of an example of a method of removing projection artifacts in an OCT angiogram of the choriocapillaris.

A fifth example is a method of removing projection artifacts from an OCT angiogram of a choriocapillaris layer 1300 as outlined in FIG. 5 herein. This example involves generating an en face inner retina angiogram 1302, applying a filter such as a Gaussian or low pass filter 1304 to the en face inner retina angiogram. The filter removes small inner retinal vessels. A binary large inner retinal vessel mask is generated from the filtered inner retina angiogram 1306. The example further involves generating an en face choriocapillaris angiogram 1308, removing projection artifacts in the en face choriocapillaris angiogram by multiplying each element of the mask matrix by the corresponding element in the choriocapillaris layer matrix 1310. The result can be output as a matrix presenting artifact-free en-face choriocapillaris flow or an artifact-free en-face choriocapillaris flow angiogram 1312. The information in the artifact-free en-face choriocapillaris angiogram can be used to remove projection artifacts in the cross-sectional choriocapillaris angiogram 1314, thereby generating an artifact-free cross-sectional choriocapillaris angiogram 1316.

Figure 6:
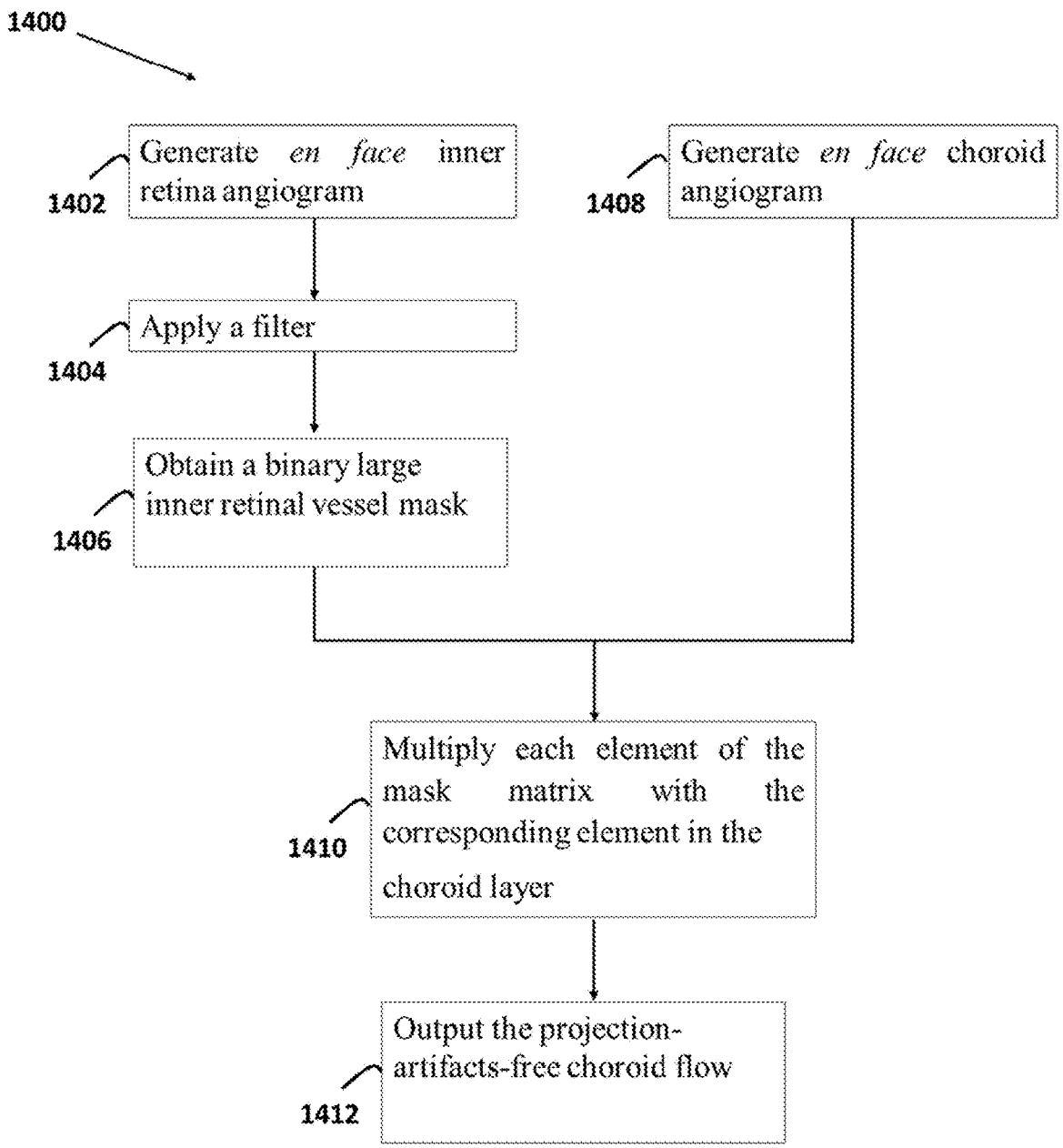
FIG. 6 is a flow chart of an example of a method of removing projection artifacts in an OCT angiogram of the choroid layer.

A sixth example is a method of removing projection artifacts from an OCT angiogram of a choroid 1400 as outlined in FIG. 6 herein. This example involves generating an en face inner retina angiogram 1402, applying a filter such as a Gaussian or low pass filter 1404 to the en face inner retina angiogram. The filter removes small inner retinal vessels. A binary large inner retinal vessel mask is generated from the filtered inner retina angiogram 1406. The example further involves generating an en face choroid OCT angiogram 1408, removing projection artifacts in the en face choroid angiogram by multiplying each element of the mask matrix by the corresponding element in the choroid matrix 1410. The result can be output as a matrix presenting artifact-free en-face choroid flow or an artifact-free en-face choroid flow angiogram 1412. The information in the artifact-free en-face choroid angiogram can be used to remove projection artifacts in the cross-sectional choroid angiogram 1414, thereby generating an artifact-free cross-sectional choroid angiogram 1416.

Figure 7:
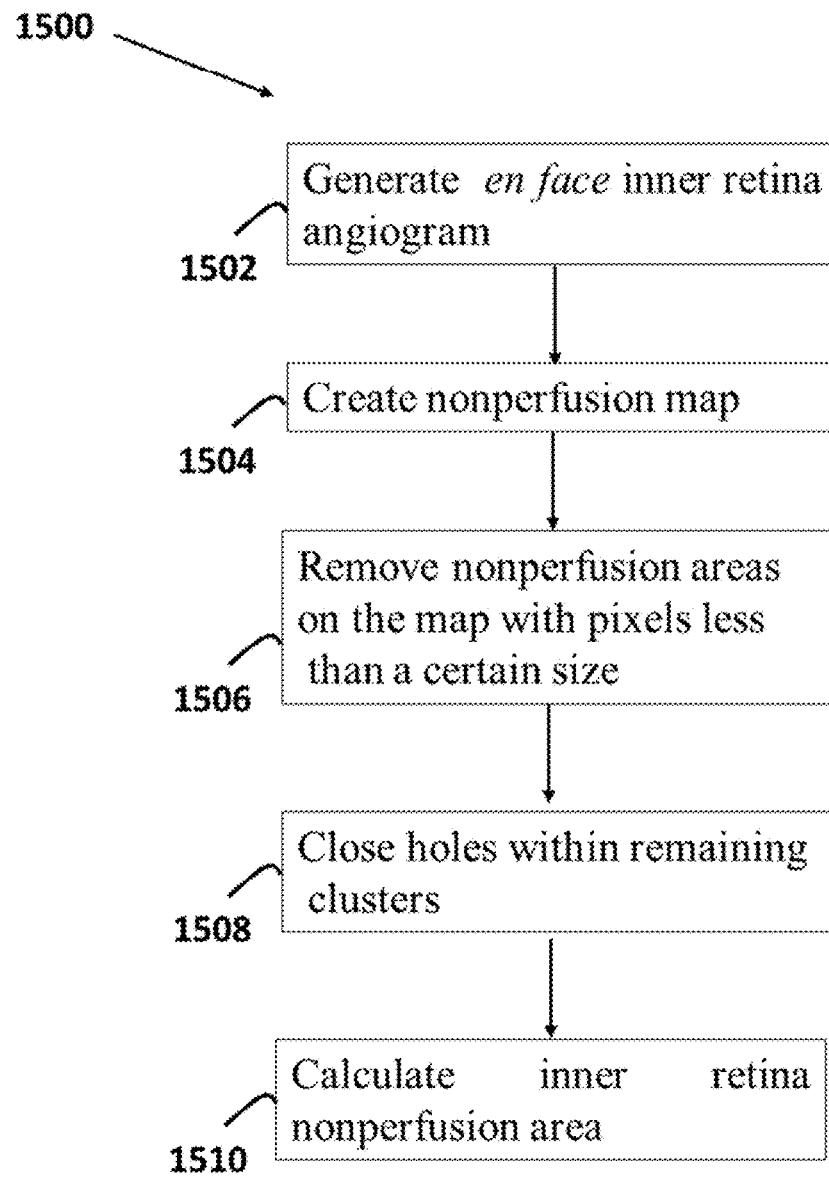
FIG. 7 is a flow chart of an example of a method of measuring a retinal nonperfusion area.

A seventh example is a method of measuring a retinal nonperfusion area 1500 as outlined in FIG. 7 herein. The method involves generating an en face inner retina angiogram as described above 1502 and creating a nonperfusion map 1504. The nonperfusion map can be created by identifying pixels with decorrelation values lower than a set cutoff point. In one example, the set cutoff point is 2.33 standard deviations below the mean decorrelation value according to a normal distribution. Nonperfusion areas with an area below a defined number of pixels are removed 1506. Holes within the remaining clusters are closed using morphological operations 1508. The retinal nonperfusion area is then calculated by summing the pixels 1510. The area can also be converted to physical dimensions such as $mm^2$.

Figure 8:
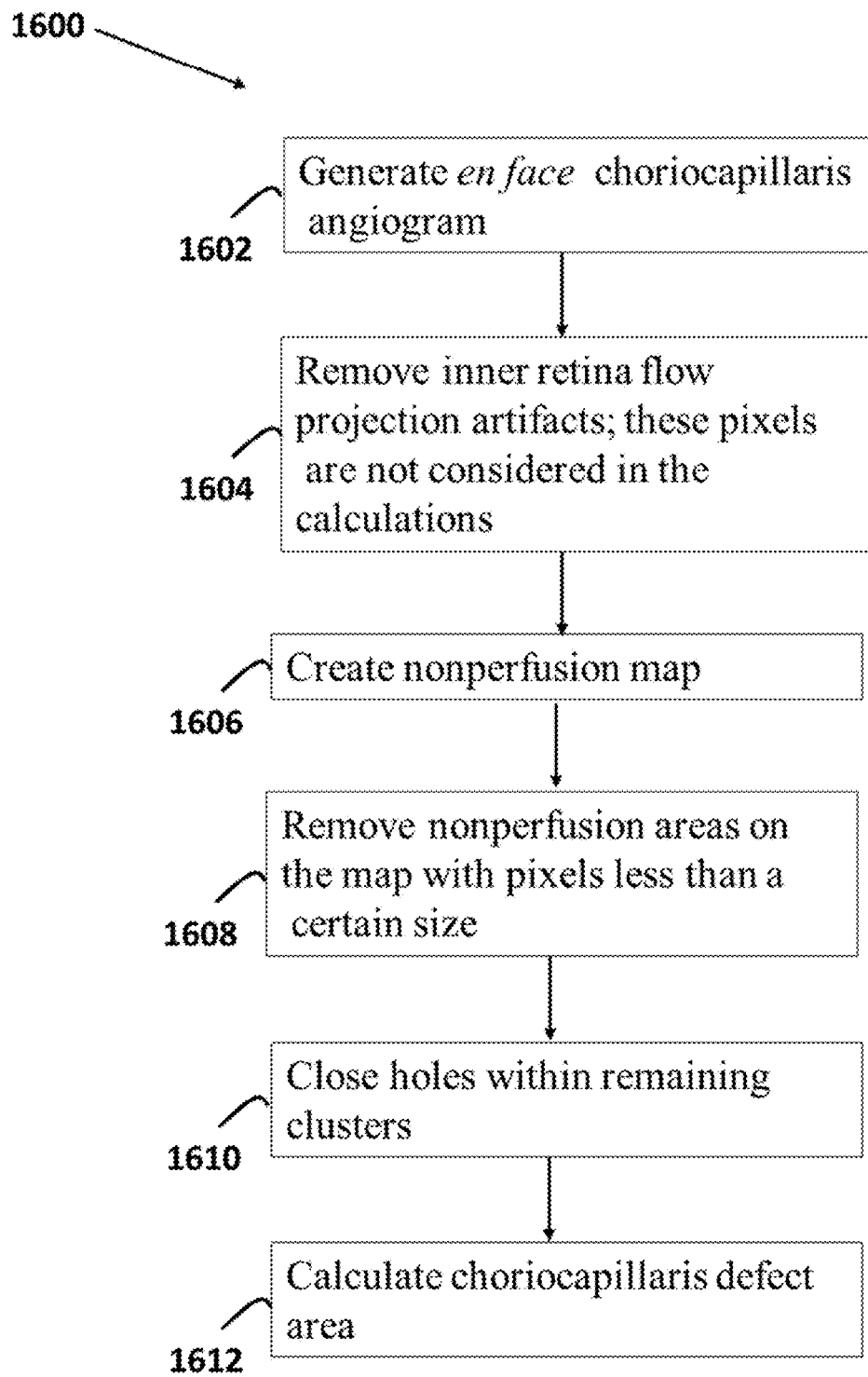
FIG. 8 is a flow chart of an example of a method of measuring a choriocapillaris defect area.

An eighth example is a method of measuring a choriocapillaris defect area 1600 as outlined in FIG. 8 herein. The method involves generating an en face choriocapillaris angiogram as described above 1602, removing inner retinal flow projection artifacts as described above 1604. Pixels that correspond to the large vessels in the inner retinal mask are not considered), and creating a nonperfusion map as described above 1606. Nonperfusion areas that fall below a defined number of pixels are removed 1608. Morphological operations close holes within the remaining clusters 1610. The choriocapillaris nonperfusion area is then calculated by summing the pixels 1612. The area can also be converted to physical dimensions such as $mm^2$.

Figure 9:
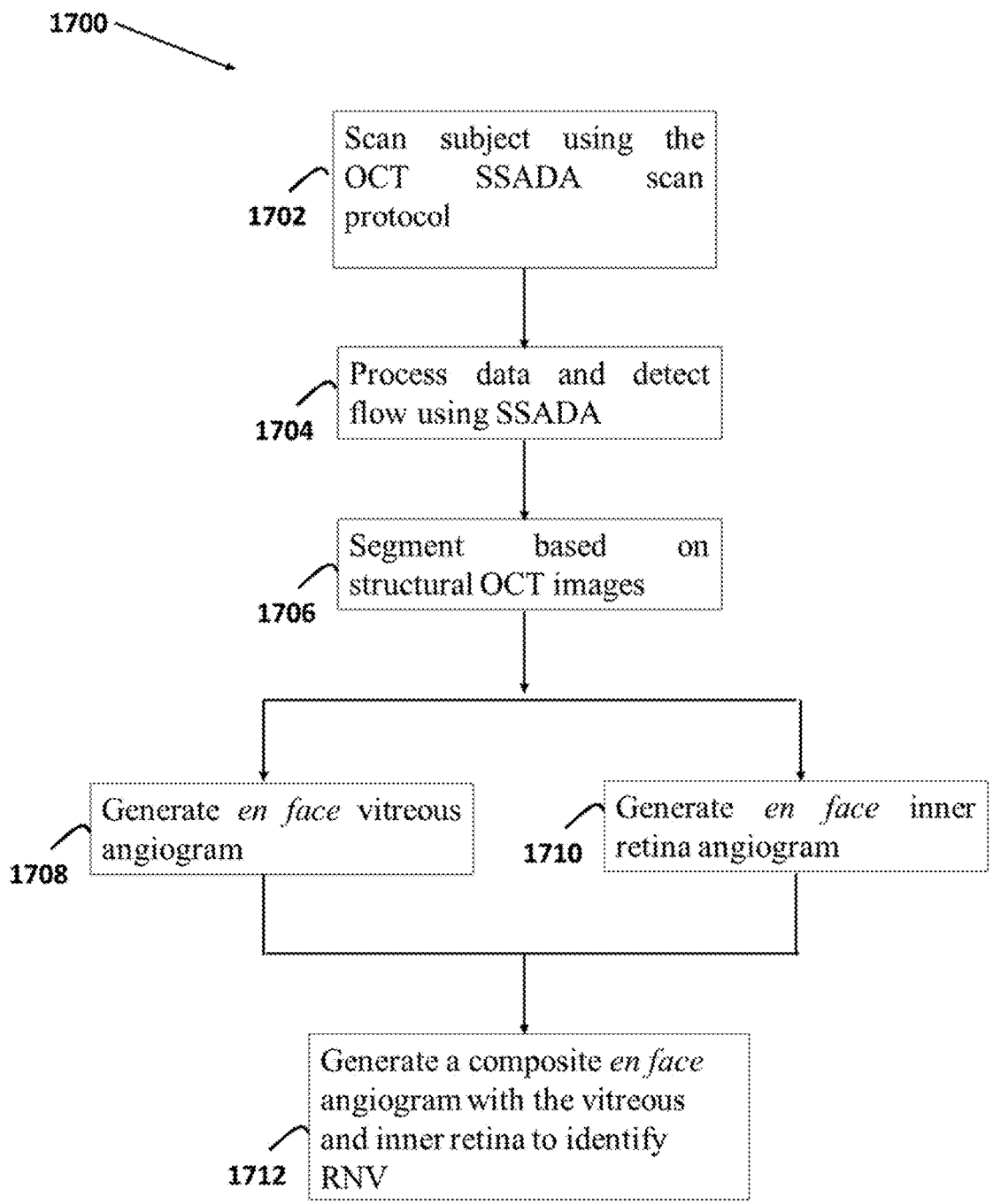
FIG. 9 is a flow chart of an example of a method of measuring retinal neovascularization.

A ninth example is a method of visualizing retinal neovascularization (RNV) using OCT 1700 as outlined in FIG. 9 herein. This example involves scanning a subject using an OCT scan protocol such as SSADA scan protocol 1702. The data is processed using, for example, the SSADA algorithm 1704 thereby generating a set of cross-sectional OCT structure images and en face structural OCT images. Each cross-sectional OCT structural image is segmented into a cross-sectional inner retina OCT structural image and a cross-sectional vitreous OCT structural image. The segmentation can be performed automatically by the software or by the end user using a graphical user interface or other input device as described above. Blood flow is detected using, for example, the SSADA algorithm 1704 thereby generating a set of cross-sectional OCT angiograms. Following the segmentation of the corresponding cross-sectional OCT structural image, each cross-sectional OCT angiogram is then segmented 1706 into a cross-sectional inner retina angiogram and a cross-sectional vitreous angiogram. The vitreous layer is defined as anterior to the inner limiting membrane (ILM) and the inner retina. The inner retinal layer is defined as above 1706. An en face vitreous angiogram is generated through by projecting the cross-sectional vitreous angiograms 1708, and an en face inner retina angiogram is generated by projecting the cross-sectional inner retina angiograms 1710. A composite en face angiogram is produced from overlaying the en face inner retina angiogram and vitreous angiogram on the structural OCT en face image 1712. The blood flow in the composite en face angiogram can be color coded 1712. In the composite angiogram, flow detected above ILM is an indication of RNV 1712.

Figure 10:
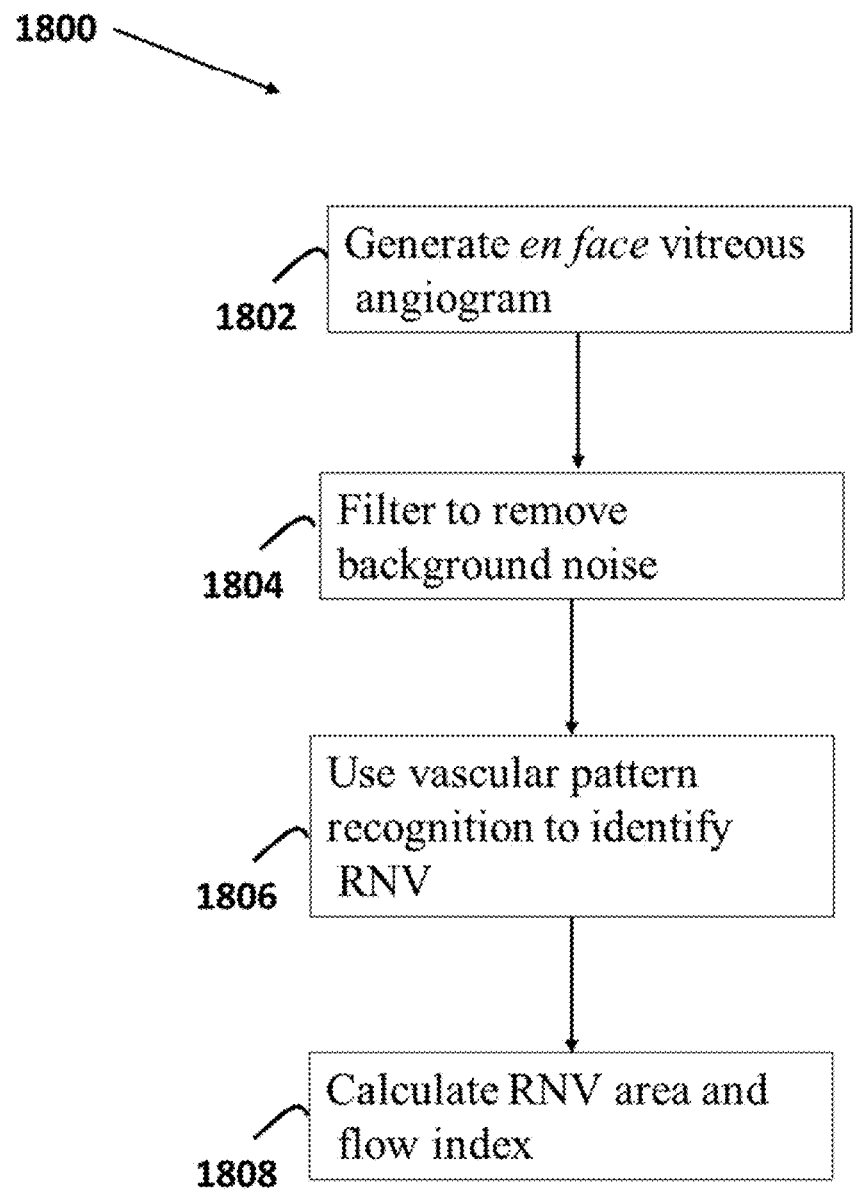
FIG. 10 is a flow chart of an example of a method of measuring a retinal neovascularization area and flow index.

A tenth example is a method of measuring retinal neovascularization (RNV) area and flow index 1800 as outlined in FIG. 10 herein. The method involves generating an en face vitreous angiogram 1802 as described above. The method further involves removing the background noise using a Gaussian or low pass filter as described above 1804, and using vascular pattern recognition as described above to identify RNV 1806. When RNV has been identified, the RNV area can be determined 1808 by summing the number of pixels for which the decorrelation value is above that of the background. The sum can be converted to physical dimensions such as $mm^2$. RNV flow index can be determined 1808 by summing the decorrelation value of the pixels which comprise the RNV and then dividing by the area of the en face vitreous angiogram.

EXAMPLES

The following examples are illustrative of disclosed methods. In light of this disclosure, those of skill in the art will recognize that variations of these examples and other examples of the disclosed method would be possible without undue experimentation.

Example 1—Quantitative Optical Coherence Tomography Angiography of Choroidal Neovascularization in Age-Related Macular Degeneration Summary Purpose:
To detect and quantify choroidal neovascularization (CNV) in patients with age-related macular degeneration (AMD) using optical coherence tomography (OCT) angiography.
Design:
Observational, cross-sectional study.
Methods:
A total of 5 eyes with neovascular AMD and 5 normal age-matched controls were scanned by a high-speed (100,000 A-scans/seconds) 1050-nm wavelength swept-source OCT. The macular angiography scan covered a 3×3-mm area and comprised 200×200×8 A-scans acquired in 3.5 seconds. Flow was detected using the split-spectrum amplitude decorrelation angiography (SSADA) algorithm. Motion artifacts were removed by 3-dimensional (3D) orthogonal registration and merging of 4 scans. The 3D angiography was segmented into 3 layers: inner retina (to show retinal vasculature), outer retina (to identify CNV), and choroid. En face maximum projection was used to obtain 2-dimensional angiograms from the 3 layers. The CNV area and flow index were computed from the en face OCT angiogram of the outer retinal layer. Flow (decorrelation) and structural data were combined in composite color angiograms for both en face and cross-sectional views.

Main Outcome Measures:

The CNV angiogram, CNV area, and CNV flow index.

Results:

En face OCT angiograms of CNV showed sizes and locations that were confirmed by fluorescein angiography (FA). Optical coherence tomography angiography provided more distinct vascular network patterns that were less obscured by subretinal hemorrhage. The en face angiograms also showed areas of reduced choroidal flow adjacent to the CNV in all cases and significantly reduced retinal flow in 1 case. Cross-sectional angiograms were used to visualize CNV location relative to the retinal pigment epithelium and Bruch's layer and classify type I and type II CNV. A feeder vessel could be identified in 1 case. Higher flow indexes were associated with larger CNV and type II CNV.

Conclusions:

Optical coherence tomography angiography provides depth-resolved information and detailed images of CNV in neovascular AMD. Quantitative information regarding CNV flow and area can be obtained. Further studies are needed to assess the role of quantitative OCT angiography in the evaluation and treatment of neovascular AMD.

Background

Age-related macular degeneration (AMD) is the leading cause of blindness in older adults of European descent (*Arch Ophthalmol* 122, 477-485 (2004); incorporated by reference herein). Neovascular AMD is an advanced form of macular degeneration that historically has accounted for the majority of vision loss related to AMD (Ferris F L et al 1984 supra). It is characterized by the presence of choroidal neovascularization (CNV) which includes abnormal blood vessels that originate from the choroid. The vessels grow through Bruch's membrane (BM) and extend into the sub-retinal pigment epithelial (RPE) or subretinal space. Choroidal neovascularization can result in hemorrhage, fluid exudation, and fibrosis, resulting in photoreceptor damage and vision loss (Ambati J et al, *Surv Ophthalmol* 48, 257-293 (2003); incorporated by reference herein). To diagnose neovascular AMD and evaluate the efficacy of treatment, determination of the presence and precise location of the CNV lesion is essential.

Fluorescein angiography (FA) and indocyanine green angiography (ICGA) are important diagnostic tools used to detect and evaluate CNV in clinical practice. Leakage of dye in the later frames of the angiogram is used to identify the presence of the CNV. Both FA and ICGA require intravenous dye injection, which can result in nausea and, rarely, anaphylaxis (Stanga P E et al, 2003 supra, Lopez-Saez M P et al, 1998 supra).

Optical coherence tomography (OCT) generates cross-sectional images by measuring the echo time delay and magnitude of backscattered light (Huang D et al, *Science* 254, 1178-1181 (1991); incorporated by reference herein). Optical coherence tomography has achieved micrometer-level axial resolution in cross-sectional retinal imaging. The earliest retinal OCT imaging for studying neovascular AMD was based on first-generation time-domain OCT technology, which has limited speed and sensitivity (Hee M R et al, *Ophthalmology* 103, 1260-1270 (1996); Do D V et al, *Ophthalmology* 119, 771-778 (2012); and Coscas F et al, *Am J Ophthalmol* 144, 592-599 (2007); all of which are incorporated by reference herein). Spectral-domain OCT has greatly improved speed and sensitivity and is able to detect small changes in the morphology of the retinal layers and CNV activity in neovascular AMD (Framme C et al, *Invest Ophthalmol Vis Sci* 51, 1671-1676 (2010) and Sayanagi K et al, *Ophthalmology* 116, 947-955 (2009); both of which are incorporated by reference herein). More recently, swept-source OCT has demonstrated improved ranging depth by using a rapidly tuned laser and a longer wavelength (1050-nm spectral range) allowing for improved imaging beneath the RPE (de Bruin D M et al, *Invest Opthalmol Vis Sci* 49, 4545-4552 (2008); incorporated by reference herein). Therefore, this OCT modality may allow for better visualization of the CNV beneath the RPE.

Structural OCT, using any technology, is only sensitive to backscattering light intensity and cannot detect blood flow information. Because of this limitation, structural OCT cannot reliably discriminate vascular tissue from the surrounding tissues; thus, the precise location and activity of the CNV cannot be determined. Since 2007, several phase-based (e.g., Doppler shift (Hong Y J et al, *Opt Express* 20, 2740-2760 (2012) and Grulkowski I et al, *Opt Express* 17, 23736-23754 (2009), both of which are incorporated by reference herein); Doppler variance (Liu G et al, *Opt Express* 19, 3657-3666 (2011) and Wang L et al, *Opt Commun* 242, 345-350 (2004); both of which are incorporated by reference herein) and phase-variance (Fingler J et al, *Opt Express* 2, 1504-1513 (2011) and Kim D Y et al, *Biomed Opt Express* 2, 1504-1513; both of which are incorporated by reference herein)) and intensity-based (e.g., speckle variance (Hendargo H C 2013 supra; Mariampillai A et al, *Opt Lett* 35, 1257-1259 (2010); incorporated by reference herein; and Mariampillai A et al 2008 supra) and decorrelation (Enfield J et al, 2011 supra and Johnathan E et al, *J Biophotonics* 4, 583-587 (2011); incorporated by reference herein). OCT angiography methods have been described for 3-dimensional (3D) noninvasive vasculature mapping at the microcirculation level. Miura et al 2011 supra and Hong et al 2013 supra recently demonstrated Doppler optical coherence angiography for imaging 3D views of ocular vascular pathology in polypoidal choroidal vasculopathy and exudative macular diseases, respectively.

Recently, the split-spectrum amplitude-decorrelation angiography (SSADA) algorithm was developed to improve the signal-to-noise ratio of flow detection (Jia Y et al, *Opt Express* 20, 4710-4725 (2012); incorporated by reference herein) This technique enables OCT angiography within a practical image acquisition time (in seconds) using a prototype that is only slightly faster than the newest generation of commercial systems. The first clinical study for demonstrating ocular vascular disturbances in glaucoma was also recently performed (Jia Y et al, *Biomed Opt Express* 3, 3127-3137 (2012); incorporated by reference herein)

The use of OCT angiography using the SSADA algorithm to investigate CNV associated with neovascular AMD is described herein. A descriptive case series of neovascular AMD is presented to describe the usefulness of OCT angiography for visualizing 3D vascular architecture and quantifying the blood flow within CNV.

Methods:

Patients were selected from clinical retina practices at the Casey Eye Institute. Patients diagnosed with neovascular AMD underwent a comprehensive eye examination and routine diagnostic evaluation consisting of color fundus photography, FA, and OCT (Spectralis; Heidelberg Engineering, Heidelberg, Germany). Patients aged more than 50 years with the presence of drusen and treatment-naïve CNV confirmed by fluorescein dye leakage on angiogram and the presence of 1 of the following on OCT: subretinal fluid, intraretinal fluid, or sub-RPE fluid were included in the study. Patients with subretinal hemorrhage of >50% of the CNV lesion, visual acuity <20/200, and media opacity interfering with OCT image quality, such as cataracts were excluded.

The OCT angiograms of normal subjects (aged 40-79 years) from a separate study, the Functional and Structural Optical Coherence Tomography for Glaucoma, were used as controls in this study. Inclusion criteria from that study included vision >20/40, no ocular surgery other than previous cataract surgery, and no eye disease affecting vision. A total of 24 normal control subjects' images were used for normative retinal thickness measurements, and 5 control subjects (aged >60 years) underwent OCT angiography processing.

Optical Coherence Technology Angiography:

The prototype high-speed swept-source OCT system was built by the Laser Medicine and Medical Imaging Group at the Massachusetts Institute of Technology and followed the configuration published by Potsaid et al *Opt Express* 18, 20029-20048 (2010) which is incorporated by reference herein. The device operated at an axial scan speed of 100 kHz using a swept-source cavity laser operating at 1050 nm with a tuning range of 100 nm. A resolution of 5.3 mm axially and 18 mm laterally at an imaging depth of 2.9 mm in tissue was achieved. The ocular light power exposure was 1.9 mW, which was within the American National Standards Institute safety limit (*American National Standard for the Safe Use of Lasers, Laser Institute of America*, Z136 (2007); incorporated by reference herein).

A 3×3-mm scanning area centered on the fovea was captured for blood flow measurements. In the fast transverse scanning direction, 200 axial scans were sampled along a 3-mm region to obtain a single B-scan. Eight consecutive B-scans (M-B frames) were captured at a fixed position before proceeding to the next sampling location. A total of 200 locations along a 3-mm region in the slow transverse direction were sampled to form a 3D data cube. With a B-scan frame rate of 455 frames per second, the 1600 Bscans in each scan were acquired in approximately 3.5 seconds. Four volumetric raster scans, including 2 horizontal priority fast transverse (x-fast) scans and 2 vertical priority fast transverse (yfast) scans, were obtained consecutively in 1 session.

The SSADA algorithm was used to distinguish blood flow from static tissue as described in Jia et al, *Opt Express* 2012 supra. As seen in real-time OCT structural images, the amplitude of the signal returning from nonstatic tissue varies rapidly over time. By calculating the decorrelation of signal amplitude from consecutive B-scans, a contrast between static and nonstatic tissue is created that allows for the visualization of blood flow. However, decorrelation also can be generated by bulk (nonflow) eye motion. The SSADA algorithm was developed to minimize bulk axial motion noise due to orbital pulsation by splitting the spectrum and thereby lengthening the axial resolution element. In addition, the algorithm incorporated 3 steps to further remove motion artifacts within each angiography scan. First, using outlier analysis, the decorrelation frames with excessive median decorrelation values (i.e., frames corrupted by saccadic and micro-saccadic eye movements) were removed at each M-B scan position, and the remaining individual frames were averaged to obtain the final average decorrelation flow image. Second, if the number of remaining individual frames is less than 3 for averaging, the average decorrelation image at this location is replaced by the spatial neighbors. Third, the median decorrelation (an estimate of bulk motion effect) was calculated for each average decorrelation frame and then subtracted from it. This sets the decorrelation value for bulk tissue to approximately zero.

Physical flow phantom calibration experiments have been described in previous references (Tokayer J et al, *Biomed Opt Express* 4, 1909-1924 (2013) and Liu G et al, *Biomed Opt Express* 3, 2669-2680 (2013); both of which are incorporated by reference herein). Decorrelation can be considered as a metric for measuring fluctuation in the backscattered OCT signal amplitude (intensity) that does not depend on the average signal level. To be specific, the blood flow results in fluctuation in the amplitude of OCT fringes (speckle) as red blood cells move within a particular voxel. Thus, the 8 M-B frames contain fluctuating values of OCT output intensities at any given voxel in the flow of blood, and decorrelation is defined such that fluctuating intensities yield high decorrelation values (approaching 1.0). Pixels in the M-B frames that represent static tissue have constant intensities, and thus yield small decorrelation values (approaching 0). The faster the blood particles that move across the laser beam, the higher the decorrelation of the received signals within a velocity range set by the scan parameters. In other words, decorrelation is approximately linear to flow velocity (the distance traveled by red blood cells flowing across the light beam within a unit time). However, beyond a saturation velocity that is defined by the time interval between consecutive OCT M-B frames, the decorrelation increases more slowly with velocity and eventually reaches an upper boundary. This saturation velocity should be approximately 0.3 to 0.7 mm/second according to previous references describing physical phantom experiments, accounting for a wavelength of 1050 nm and inter-M-B frame interval of 2 milliseconds. The minimum velocity is approximately 0.02 mm/second according to the phantom calibration. This is determined by the threshold decorrelation value 0.09, which is 2 standard deviations above the mean decorrelation value in the noise region, the central foveal avascular zone in normal eyes.

Motion artifacts were further corrected by applying an image registration algorithm that registered 4 orthogonal raster scanned volumes (Kraus M F et al, *Biomed Opt Express* 3, 1182-1199 (2012); incorporated by reference herein). Motion correction was first performed on the structural OCT data. The motion correction algorithm generated 3D displacement fields that map A-scans from the input volumes into a common motion-corrected space. The same displacement fields were applied to the decorrelation (flow) data to produce motion-corrected flow data volumes. Flow data from 4 input volumes were weighted and merged, improving the signal-to-noise ratio in the flow signal and reducing the flow measurement variation due to local flow changes caused by the cardiac cycle.

To enhance visualization, the 3D angiogram was separately projected into en face views (FIG. 11) in 3 layers using an automated algorithm (Tan O et al, *Ophthalmology* 116, 2305-2314 (2009) and Tan O et al, *Ophthalmology* 115, 949-956 (2008); both of which are incorporated by reference herein. The inner retinal layer was defined from the internal limiting membrane to the outer boundary of the outer plexiform layer (OPL). Thus defined, the inner retina should contain all of the normal retinal vasculature. The outer retinal layer was defined from the outer OPL to the BM. Because the outer retina is normally avascular, any flow in this layer could be interpreted as CNV. The choroidal layer was defined as below BM. All of these boundaries were identified through the analysis of the reflectance and reflectance-gradient profiles in depth. Clinician's interpretation and manual identification of BM and the OPL was necessary when pathologies such as pigment epithelial detachment (PED) and intraretinal fluid obscured the outer retinal landmarks (AMD case 3). Separate en face images of the inner retina, outer retina, and choroid were presented in a sepia color scale. A composite view was developed, where each layer was assigned a different color (FIG. 11C) to aid with visualization as follows. The inner retina contained normal retinal circulation and was coded purple. The outer retinal layer contained any potential CNV and was coded yellow. The choroid layer was coded red.

Structural OCT features were added to OCT angiography with composite en face view and color coding demonstrating subretinal fluid (dark blue) (FIG. 12G) and intraretinal cysts (light blue) (FIG. 13) These two types of fluid are both detected using a level-set segmentation method (Chan T F and Vese L A, *IEEE Trans Image Process* 10, 266-277 (2001); incorporated by reference herein) because the reflectance of cysts and subretinal fluid is significantly lower than the surrounding tissue in the retina. On the basis of the difference among their position, shape, and size, these fluid regions can be classified as intraretinal or subretinal. In addition, the variation in retinal thickness was calculated, normalized by the normal retina thickness range, and presented as a retinal thickness deviation map. For the purpose of this pilot study, an estimate of normal retinal thickness with the prototype OCT was obtained from 24 normal eyes from 24 subjects.

The cross-sectional angiogram (FIG. 11B) showed flow projection artifacts on the photoreceptor inner segment/outer segment boundary and RPE. The projection artifacts were due to fluctuating shadows cast by flowing blood in large inner retinal vessels that cause variation in the reflected signal in deeper layers. The signal variation was detected as a decorrelation and could not be differentiated from true flow on its own. However, these artifacts were removed from under the flow pixels in the inner retina. To remove flow projection artifacts from superficial retinal blood vessels to the outer retina, a method was developed. A binary large inner retinal vessel map was generated by applying a 30×30 pixel Gaussian filter. This filter removed small inner retinal vessels and masked the outer retina flow map, thus enabling the subtraction of large vessel projections. A binary outer retinal flow map was then generated by applying a 10×10 pixel Gaussian filter to remove remaining noise and mask the outer retinal flow map again to obtain a clean map. After these artifacts were removed by the mask subtraction operation, there were no longer any flow artifacts in the normally avascular outer retina, as shown in the cross-sectional color angiogram (FIG. 11C) and the en face angiogram of the outer retina (FIG. 11E).

To quantify the blood flow within the CNV, the CNV area and flow index were calculated from the 2-dimensional maximum projection outer retina CNV angiogram. The CNV area was calculated by multiplying the number of pixels (for which the decorrelation value was above that of the background) and the pixel size. The CNV flow index was the average decorrelation value in the CNV region, given by, Equation 1 below:

$$\frac{\int_A D \cdot V dA}{\int_A dA} (V = 1 \text{ if vessel}, V = 0 \text{ if not}) \qquad \text{Equation 1}$$

where D is the decorrelation value acquired by SSADA. V is 1 when the decorrelation value was above the background; otherwise, V is 0. Flow index is a dimensionless parameter between 0 and 1 that is proportional to the density of blood vessels (fractional area occupied by vessels) and the velocity of blood flow in the CNV region.

Results:

The OCT angiograms of 5 neovascular AMD eyes were compared with 5 normal eyes. The CNV area and flow index were calculated from all neovascular AMD cases. None of the 5 normal cases had flow detected in the outer retina, and CNV area and flow index were zero. A representative normal control case and 3 of the neovascular AMD cases are presented. Normal control case: A 69-year-old woman with no ocular disease served as a control case. The inner retinal angiogram (FIG. 11D) showed the normal retinal circulation with a small foveal avascular zone of approximately 0.6 mm in diameter. The absence of any flow in the outer retinal layer (FIG. 11E) allowed easy detection of CNV in the cases to be shown later. The absence of blood flow in the outer retina was noted in all 5 normal control participants. The flow in the inner choroid\ was nearly confluent (FIGS. 11C, 11F) and masked the vascular patterns in the outer choroid and sclera in the en face angiogram (FIG. 11F). The signal voids in the larger vessels in the outer choroid were due to the high flow velocity (FIGS. 11A-11C).

Age Related Macular Degeneration Case 1:

A 65-year-old woman noted vision loss in her right eye for 1 month. Visual acuity measured 20/100 in the right eye. Fundus photography (FIG. 12A) showed drusen and a small subretinal hemorrhage associated with a gray subretinal lesion just nasal to the fovea. Fluorescein angiography (FIGS. 12B, 12C) revealed early hyperfluorescence with late leakage consistent with classic CNV.

Optical coherence tomography angiography showed a normal retinal circulation (FIG. 12D, 12H). The outer retinal OCT angiogram (FIGS. 12E, 12H) showed high flow in a CNV network in a pattern strikingly similar to the early phase of FA. The cross-sectional color OCT angiogram (FIG. 12G) showed the CNV to be underneath the RPE and above the BM, indicating type I CNV. The subretinal hemorrhage above the CNV (FIG. 12G) did not seem to obscure the CNV on the FA or OCT angiograms (FIGS. 12E, 12H).

The en face OCT angiogram of the choroid (FIG. 12F) showed loss of choriocapillaris revealing deeper, larger choroidal vessels (compare with normal choroid in FIG. 11F). An area inferotemporal to the CNV had particularly low flow in both the choriocapillaris and the deeper choroid (FIG. 12F, green outline). This low flow choroidal region had high OCT reflectance signal (FIG. 12G, green arrow); therefore, the reduced flow was not caused by a shadow artifact.

The composite en face OCT angiogram (FIG. 12H) showed that the CNV was at the superonasal edge of the fovea avascular zone (FAZ) and that subretinal fluid was accumulated next to the CNV. The OCT retinal thickness map (FIG. 12I) showed retinal thickening over the CNV that was primarily due to the inclusion of subretinal hemorrhage (FIG. 12G) in the retinal thickness measurement and an element of retinal edema inferior to the CNV. These en face OCT views combined angiographic (CNV size, location, flow) and structural information (fluid, edema) that would be useful for clinical management.

Age Related Macular Degeneration Case 2:

A 76-year-old woman noticed vision loss in her left eye for 1 week. Visual acuity measured 20/30, and fundus examination (FIG. 13A) of the left eye revealed drusen and a gray/green lesion in the temporal macula with associated subretinal hemorrhage. Early frames of the FA revealed a hyperfluorescent vascular network I the temporal macula with late leakage (FIGS. 13B, 13C).

The OCT angiography showed details of the CNV structure, with a central feeder vessel from which radiated thick core vessels ending in fine vascular fronds (FIGS. 13E, 13J). Both the FA and OCT angiogram showed an identical CNV location, with slight notching at the superonasal edge due to shadowing from the small patch of subretinal hemorrhage. Cross-sectional OCT angiography (FIGS. 13G, 13H) revealed that most of the CNV flow was above the RPE, indicating a predominantly type II CNV. Because of the flow projection artifact, there appeared to be flow in the RPE below the CNV.

The en face OCT angiogram of the choroid (FIG. 13F) showed patchy loss of choriocapillaris, which allowed visualization of intermediate-to-large deeper choroidal vessels that were not visible in the healthy control (FIG. 11F). There were focal regions under and adjacent to the CNV where there was greatly reduced flow in both the choriocapillaris and the deeper choroid (FIGS. 13F-13H). Although some of this might be explained by shadowing under the CNV, the hypoperfused choroid adjacent to the CNV had normal OCT reflectance (FIG. 13I), suggesting that the loss of choroidal flow was real rather than an artifact.

The composite en face OCT angiogram showed that the CNV was at the superotemporal edge of the FAZ. Subretinal fluid accumulated superonasal to the CNV, and intraretinal cystic fluid accumulated above the CNV. Retinal thickening shown on the relative thickness map (FIG. 3K) correlated with the intraretinal fluid accumulation.

Age-Related Macular Degeneration Case 3:

An 88-year-old woman noted vision loss in her right eye for several months. Visual acuity in the right eye was 20/200. Fundus photography (FIG. 14A) demonstrated chronic geographic atrophy in the superior nasal macula with new subretinal hemorrhage and an associated RPE tear temporal to the geographic atrophy. Fluorescein angiography showed late leakage consistent with a CNV (FIGS. 14B, 14C). However, the location of the CNV was unclear because of blocking from the subretinal hemorrhage. Hypofluorescence from the scrolled RPE and hyperfluorescence-associated geographic atrophy were evident.

The inner retinal angiogram in this case (FIG. 14D) showed an apparent reduction in inner retinal blood flow that may have indicated retinal atrophy. This patient had difficulty with fixation, and slight motion artifacts (horizontal and vertical dark lines) were evident despite the use of 3D registration software.

The OCT angiography of the outer retina (FIGS. 14E-14H) showed a distinct CNV adjacent to the subretinal hemorrhage. The nasal edge of the CNV was blocked from view where the subretinal hemorrhage was thicker and cast a shadow. The cross-sectional OCT angiogram (FIG. 14G) revealed high CNV flow at the edge of the RPE tear. Flow was detected both above and below the RPE, indicating a combined type I and type II lesion. In addition to the CNV, there was accumulation of a large amount of stationary (nonvascular) material under the PED.

The en face choroidal angiogram (FIG. 14F) showed reduced signal both under the PED and in the area of geographic atrophy. The area under the PED showed low reflectance on OCT cross-section (FIG. 14G) and no vascular pattern on the en face OCT angiogram (FIG. 14F). This suggested that the reduced choroidal flow was a shadow artifact associated with the PED and scrolled RPE (FIG. 14F). A similar area of blocked fluorescence was present on FA (FIG. 14B, 14C). In contrast, the area of geographic atrophy showed distinct large, deep choroidal vessels and loss of choriocapillaris.

The composite en face OCT angiogram (FIG. 14H) showed the CNV to be inferior to the FAZ and associated with a surrounding accumulation of both intraretinal and subretinal fluids. There was retinal thinning over the CNV (FIG. 14I), possibly due to focal compression from the highly elevated CNV and RPE tear (FIG. 14G). There was gross retinal thickening around the CNV (FIG. 14I) associated with fluid accumulation (FIG. 14H). The heavy accumulation of intraretinal fluid and reduced retinal blood flow visualized on the en face composite OCT angiogram may explain the poor visual acuity.

Evaluation of Choroidal Flow in Age-Related Macular Degeneration:

The OCT angiography of the choroid showed reduced inner choroidal flow in all 5 AMD cases compared with the control cases that allowed visualization of larger and deeper choroidal vessels. Conventional FA and structural OCT did not reveal geographic atrophy or other abnormalities that accounted for the choriocapillaris atrophy in most of these areas. In addition, focal areas of decreased flow in both superficial and deeper choroidal vessels were associated with CNV in all of the AMD cases, except for case 3, in whom the presence of a focal choroidal flow defect could not be determined because of shadowing by the scrolled RPE (FIG. 14F).

Quantification of the Area and Flow Index of Choroidal Neovascularization:

Quantitative measurements of CNV area and flow index are summarized in Table 1. High flow index indicated active blood flow within the CNV. Higher flow was detected with larger CNVs and those that were type II compared with type I and combined CNVs.

TABLE 1

Summary of Choroidal Neovascularization Types, Area, and Flow Index of 5 Scanned Age-related Macular Degeneration Cases

| AMD Case No. | Sex/Age | CNV Types | CNV Area (mm2) | CNV Flow Index (au) |
|---|---|---|---|---|
| 1 | Female/65 yrs | I | 0.29 | 0.127 |
| 2 | Female/76 yrs | II | 2.18 | 0.146 |
| 3 | Female/88 yrs | Combined | 0.13 | 0.13 |
| 4 | Female/85 yrs | II | 0.89 | 0.148 |
| 5 | Male/70 yrs | Combined | 0.05 | 0.12 |

Example 2—Optical Coherence Tomography Angiography Features of Diabetic Retinopathy Summary Purpose:

To describe the optical coherence tomography (OCT) angiography features of diabetic retinopathy.

Methods:

Using a 70 kHz OCT and the split-spectrum amplitude decorrelation angiography (SSADA) algorithm, 6×6 mm 3-dimensional angiograms of the macula were obtained and compared with fluorescein angiography (FA) for features catalogued by the Early Treatment of Diabetic Retinopathy Study.

Results:

OCT angiography detected enlargement and distortion of the foveal avascular zone, retinal capillary dropout, and pruning of arteriolar branches. Areas of capillary loss obscured by fluorescein leakage on FA were more clearly defined on OCT angiography. Some areas of focal leakage on FA that were thought to be microaneurysms were found to be small tufts of neovascularization that extended above the inner limiting membrane.

Conclusions:

OCT angiography does not show leakage, but can better delineate areas of capillary dropout and detect early retinal neovascularization. This new noninvasive angiography technology may be useful for routine surveillance of proliferative and ischemic changes in diabetic retinopathy.

Background

Diabetic retinopathy is a microangiopathy that causes capillary occlusion, vascular hyperpermeability, and neovascularization in the retinal vasculature (Antonetti D et al, *N Engl J Med* 366, 1227-1239 (2012); incorporated by reference herein). Detailed clinical examination for grading disease severity for risk of progression and vision loss is the standard of care but ophthalmic angiography has played a critical role in understanding and care of the disease. Early Treatment of Diabetic Retinopathy Study (ETDRS) examined the fluorescein angiographic features of the posterior pole of patients with non-proliferative diabetic retinopathy and correlated the specific features with their risk of disease progression (EDTRS Research Group, *Ophthalmol* 98, 834-840 (1991); EDTRS Research Group, *Ophthalmol* 98, 807-822 (1991); incorporated by reference herein). Fluorescein angiography (FA) is also used to identify retinal neovascularization (RNV) in situations where clinical examination cannot detect RNV or distinguish from other anomalous appearing vessels on the retinal surface.

While angiography provides valuable additional information compared to clinical examination or fundus photography, it is not part of the routine diabetic eye examination. FA requires venipuncture and intravenous injection of a dye that has a moderate risk of nausea and a rare but well documented risk of anaphylaxis and death (Bloome M A, *Vis Res* 20, 1083-1097 (1980); incorporated by reference herein). Also, a standard protocol FA acquires images over 10 minutes with repeated exposure to a very bright light source, which can cause significant discomfort for patients.

Optical coherence tomography (OCT) angiography, an imaging technique that uses decorrelation between resampled images to detect flow to construct 2- and 3-dimensional images of blood flow within the eye, offers an alternative angiographic technique without some of the drawbacks of FA. In particular, the split-spectrum amplitude decorrelation algorithm (SSADA) can be used to detect flow signals for angiography efficiently (Jia et al, (2012) supra); incorporated by reference herein). Applying this algorithm, an OCT angiogram in areas up to 6×6 mm area can be acquired in 3.5 seconds without intravenous injection. This Example describes features of diabetic retinopathy as seen on OCT angiography.

Methods:

Patients were selected from the Retina Division of the Casey Eye Institute for the diagnosis of proliferative diabetic retinopathy, clear media, and the ability to fixate. They underwent comprehensive ophthalmic examination and FA. Three dimensional (3D) OCT angiography scans were acquired over 6×6 mm regions using a commercially available 70 kHz OCT (RT-VUE XR, Optovue, Fremont, Calif.) with a scan pattern of 5 repeated B-scans at 216 raster positions and each B-scan consisting of 216 A-scans. Flow was detected with the split-spectrum amplitude decorrelation angiography (SSADA) algorithm (Jia et al, (2012) supra; Jia Y et al, (2014) supra); incorporated by reference herein) and motion artifacts were removed by 3D orthogonal registration and merging of 2 scans. A retinal angiogram was created by projecting the flow signal internal to the Bruch's membrane in en face orientation. The signal above the internal limiting membrane (ILM) was further segmented to isolate retinal neovascularization. Specific features seen on OCT angiogram were then compared to FA features of the same area. Images were examined for classic features of diabetic retinopathy, such as microaneurysms (MAs) and RNV, as well as gradable angiographic characteristics as described by the ETDRS Report No. 11, including foveal avascular zone (FAZ) enlargement, capillary dropout, and arteriolar abnormalities.

Results:

Four patients with proliferative diabetic retinopathy or diabetic macular edema were imaged for the study. Their characteristics are summarized in Table 1.

TABLE 1

Patient Characteristics

| Subject | Age | Gender | DM Type | Imaged Eye | Visual Acuity |
|---------|-----|--------|---------|------------|---------------|
| 1 | 47 | M | Type 2 | OS | 20/40 |
| 2 | 28 | M | Type 1 | OS | 20/30 + 2 |
| 3 | 53 | F | Type 1 | OS | 20/50 |
| 4 | 41 | F | Type 2 | OD | 20/20 |

OD, right eye;
OS, left Eye

Foveal Avascular Zone Size and Shape:

For all eyes imaged, the foveal avascular zone (FAZ) size and shape were gradable according to the ETDRS grading criteria using OCT angiography. The OCT angiogram disclosed the area of perifoveal capillary loss that corresponded well to FA. FIG. 15 shows an OCT angiogram with superposed ETDRS grid that shows that the size of the FAZ is between 300 microns radius (dotted circle) and 500 micron (solid inner circle). At the same magnification, it was easier to grade the OCT angiogram for FAZ characteristics than the FA, as the capillaries were seen at a higher contrast on OCT angiogram.

In one case, the foveal avascular zone was difficult to grade on FA as the capillary details were obscured by leakage even in early transit (FIG. 16). With the OCT angiography, the details were not affected by leakage and the FAZ size and shape could be easily graded.

Capillary Dropout and Arteriolar Characteristics:

Areas of capillary drop out beyond the FAZ were readily identified with OCT angiogram in all eyes. FIG. 17 demonstrates good correlation in the areas of capillary drop out between the OCT angiogram and the FA. In this case, OCT angiography identified additional areas of capillary drop out not seen on FA as early diffuse fluorescein leakage made some areas of capillary dropout indistinguishable from areas with intact capillaries in the FA. In other cases, areas of capillary drop out that were obvious on OCT angiogram were difficult to resolve with FA (Upper right hand corner of FIG. 16 is an example.). In this series, OCT angiography was more consistent in demonstrating presence or absence of retinal capillaries than FA.

An area of intraretinal microvascular abnormality (IRMA), characterized by dilated terminal vessels surrounded by an area of capillary loss was identified with OCT angiography as well as FA. The exact shape of the IRMA differed slightly between two images (FIG. 16). Arteriolar narrowing and wall staining seen on FA was seen as extreme attenuation of vessel caliber on OCT angiography (FIG. 17). Microaneurysms and Neovascularization:

OCT angiography with 6×6 mm field of view could not identify microaneurysms seen on the FA. (FIG. 16). On the FA of one patient, areas of focal hyperfluorescence with leakage in the perifoveal area that were thought to be large microaneurysms were determined to be small tufts of neovascularization on OCT angiography. (FIG. 17) With the segmentation of the flow signal at the level of the ILM and projecting the signal in the cross sectional orientation, it was evident that these lesions were vertical RNV protruding into the vitreous (FIGS. 15, 16, and 17).

While RNV close to the ILM were readily identified, flow signal from the vessels that were highly elevated from the retinal surface displayed as shadows rather than flow signals because the most elevated portion of RNV outside the depth range of OCT imaging (FIG. 18).

Features described in ETDRS that are inherently specific to fluorescein angiography and unlikely to have correlates in OCT angiography, such as retinal pigment epithelial defects, severity of late fluorescein leakage and determining their source were not evaluated for this study.

TABLE 2

Optical Coherence Tomography Angiographic Findings

| Subject | FAZ Size (μ) | Outline of FAZ | Capillary Drop Out | Neovascularization and Other Vascular Abnormalities |
|---|---|---|---|---|
| 1 | <300 | Questionable | Superotemporal and inferotemporal | Isolated NVE temporally, IRMA infratemporally |
| 2 | 300-500 | Less than half | Central, and extensive loss throughout temporal macula | Perifoveal NVE and NVD (not shown) Arteriolar pruning temporally Arteriolar narrowing and staining superiorly |
| 3 | 300-500 | More than half | Central, superotemporal and inferotemporal | Extensive NVD, NVE inferiorly |
| 4 | 300-500 | More than half | Central | Extensive NVD, small tufts of NVE along temporal arcades |

FAZ = foveal avascular zone,
NVE = neovascularization elsewhere,
IRMA = intraretinal microvascular abnormality,
NVD = neovascularization at the disc Example 3—Quantitative Optical Coherence Tomography Angiography of Vascular Abnormalities in the Living Human Eye Summary Retinal vascular diseases are important causes of vision loss. A detailed evaluation of the vascular abnormalities facilitates diagnosis and treatment in these diseases. Optical coherence tomography (OCT) angiography using the highly efficient split-spectrum amplitude decorrelation angiography algorithm offers an alternative to conventional dye-based retinal angiography. OCT angiography has several advantages, including three-dimensional visualization of retinal and choroidal circulations (including the choriocapillaris) and avoidance of dye injection related complications. Results from six illustrative cases are reported. In diabetic retinopathy, OCT angiography can detect neovascularization and quantify ischemia. In age-related macular degeneration, choroidal neovascularization can be observed without the obscuration of details caused by dye leakage in conventional angiography. Choriocapillaris dysfunction can be detected in the non-neovascular form of the disease, furthering the understanding of pathogenesis. In choroideremia, its ability to show choroidal and retinal vascular dysfunction separately may be valuable in predicting progression and assessing treatment response. OCT angiography shows promise as a non-invasive alternative to dye-based angiography for highly detailed, in vivo, three-dimensional, quantitative evaluation of retinal vascular abnormalities.

The cases presented in the following Examples utilize an amplitude-based OCT angiography method called split-spectrum amplitude-decorrelation angiography (SSADA) (Jia Y et al, 2012 supra)). The SSADA algorithm detects motion in blood vessel lumen by measuring the variation in reflected OCT signal amplitude between consecutive cross-sectional scans. SSADA is a method of processing an OCT signal to enhance flow detection and to reject axial bulk motion noise. Compared to the full-spectrum amplitude method, SSADA using four-fold spectral splits improved the signal-to-noise ratio (SNR) by a factor of two, which is equivalent to reducing the scan time by a factor of four (Jia Y et al, 2012 supra). More recent SSADA implementations use even more than a four-fold split to further enhance the SNR of flow detection. This highly efficient algorithm generates high quality angiograms of both the retina and choroid. The angiograms have capillary-level detail and can be obtained with currently available commercial OCT systems.

Additionally described in the Examples below are techniques designed to help clinicians rapidly interpret OCT angiograms and to easily identify pathological vascular features. These techniques include 1) separation of the 3D angiogram into individual vascular beds via segmentation algorithms; 2) presentation of en face OCT angiograms, analogous to traditional angiography; 3) creation of cross-sectional structural OCT images with superimposed OCT angiograms to help correlate anatomical alterations with vascular abnormalities; and 4) quantification of neovascularization and capillary dropout in both the retinal and choroidal circulation.

Methods:

Human Subjects Imaging:

Study subjects were enrolled after informed consent in accordance with an Institutional Review Board/Ethics Committee approved protocol at Oregon Health & Science University and at the Massachusetts Institute of Technology in compliance with the Declaration of Helsinki. Healthy participants or patients with a diagnosis of retinal disease (diabetic retinopathy/AMD/choroideremia) were selected from the Retina Division of the Casey Eye Institute for their clear media and ability to fixate. In total, 15 healthy subjects, 14 diabetic retinopathy, 26 AMD, and 3 choroideremia patients were enrolled. To better demonstrate the potential clinical application of this novel OCT methodology, six cases with characteristic pathological and clinical features were selected for this article.

Color fundus and optic disc photographs were acquired with Zeiss fundus cameras (FF3 for FIGS. 20A and 22A, and FF450 for FIG. 23; Carl Zeiss Meditec, Inc., Dublin, Calif., USA) and the Optos 200Tx confocal scanning laser ophthalmoscope (cSLO) (FIG. 21A; Optos PLC, Dunfermline, Scotland). For fluorescein angiography, 10% sodium fluorescein in water (500 mg/5 mL) was injected intravenously using a 23- or 25-gauge needle, followed by a flush of normal saline. Fluorescein angiography was performed using either the Optos 200Tx cSLO (FIGS. 20A and 21B) or the Spectralis HRA+OCT cSLO (FIG. 22B; Heidelberg Engineering, Heidelberg, Germany). For both cSLO devices, a 488-nm wavelength laser excited the fluorescein, and a barrier filter at 500 nm separated the excitation and emission light. The fluorescein autofluorescence image in FIGS. 23 and 24 was also acquired using the Spectralis HRA+OCT cSLO. These procedures, imaging systems, and contrast dyes are approved by the Food and Drug Administration.

OCT Systems:

Two OCT systems were utilized in this study. The first was a custom-built swept-source OCT instrument (Jia Y et al, *Ophthalmology* 121, 1435-1444 (2014A); Jia Y et al, *Ophthalmology* 121, 1322-1332 (2014); and Choi W et al, *PLoS ONE* 8, e81499 (2013); all of which are incorporated by reference herein). The device operated at an axial scan rate of 100 kHz using a swept-source cavity laser operating at ~1050 nm with a sweep range of 100 nm. The instrument has a 5.3 µm axial resolution and 18 µm lateral resolution with an imaging range of 2.9 mm in tissue. The ocular light exposure was 1.9 mW, which was within the American National Standards Institute (ANSI) safety limit. (44) The second OCT system was a commercial spectral domain OCT instrument (RTVue-XR, Optovue, Inc., Fremont, Calif., USA). (36) The center wavelength was ~840 nm with a full-width-half-maximum bandwidth of 45 nm and an axial scan rate of 70 kHz.

OCT Imaging:

A 3×3- or 6×6-mm scanning area was used for OCT angiography. In the fast transverse scanning direction, 200 axial scans were sampled to obtain a single B-scan. Multiple repeated B-scans (eight for the swept-source OCT and five for the spectral OCT), were captured at a fixed position before proceeding to the next sampling location. A total of 200 locations along a 3 or 6-mm distance in the slow transverse direction were sampled to form a 3D data cube. For the swept-source system, with a B-scan frame rate of 455 frames per second, the 1,600 B-scans in each scan were acquired in ~3.5 seconds. Four volumetric raster scans, including two horizontal priority fast transverse (x-fast) scans and two vertical priority fast transverse (y-fast) scans, were obtained consecutively in one session. For the spectral domain OCT system, with a B-scan frame rate of 320 frames per second, the 1,000 B-scans in each scan were acquired in ~3.1 seconds. Two volumetric raster scans including one x-fast scan and one y-fast scan were obtained.

SSADA Processing:

The SSADA algorithm was used to distinguish blood flow from static tissue as described in detail in a previous publication (Jia Y et al 2012 supra). By calculating the decorrelation of the signal amplitude from consecutive B-scans, contrast between static and non-static tissue is created that enables visualization of blood flow. Decorrelation is a mathematical function that quantifies variation without being affected by the average signal strength, as long as the signal is strong enough to predominate over optical and/or electronic noise. Specifically, the algorithm splits the OCT image into different spectral bands, thus increasing the number of usable image frames. In the optimized SSADA technique, the OCT signal is first split into 11 spectral bands to obtain 11 low axial resolution images instead of a single image frame with high axial resolution. Each new frame has a lower axial resolution that is less susceptible to axial eye motion caused by retrobulbar pulsation. This lower resolution also translates to a wider coherence gate over which reflected signal from a moving particle such as a blood cell can interfere with adjacent structures, thereby increasing speckle contrast. In addition, each spectral band contains a different speckle pattern and independent information on flow. When amplitude decorrelation images from multiple spectral bands are combined, the flow signal is increased. By enhancing the flow signal and suppressing bulk motion noise, SSADA improves the signal-to-noise ratio of flow detection by a least a factor of two. Motion artifacts were further corrected and the flow signal increased by applying an image registration algorithm that registered orthogonal raster-scanned volumes (Kraus M F et al, *Biomed Opt Express* 3, 1182-1199 (2012); incorporated by reference herein).

OCT Angiogram Visualization and Quantification:

To enhance visualization, the 3D angiogram was separately projected as en face views in five layers: vitreous, inner retina, outer retina, choriocapillaris and deep choroid (see FIG. 19). The separated en face OCT angiography images were presented in a sepia color scale. A composite view was created, where each layer was assigned a different color. The color-coded angiogram can be superimposed on a gray-scale, cross-sectional, structural OCT image to demonstrate blood flow and structural information simultaneously. Flow projection artifacts are a common problem for existing OCT angiography techniques. To better distinguish and interpret the blood flow within different layers, a negative filter was used to mask projection artifacts from the larger caliber retinal vessels.

To quantify the blood flow within the regions of interest, the flow index, vessel density and neovascularization area were determined from the en face maximum projection angiogram. The flow index was calculated as the average decorrelation value (which is correlated with flow velocity) in the selected region, and the vessel density was calculated as the percentage area occupied by vessels and microvasculature in the selected region. For scans of the macula, flow index and vessel density can be routinely determined for the parafovea and/or perifovea. The parafovea is defined to be an annular region with an inner diameter of 0.6 mm and outer diameter of 2.5 mm centered on the FAZ. The perifovea is defined to be the annular region extending from the edge of the parafovea to an outer diameter of 5.5 mm. For a 3×3 mm scan, only the parafovea values can be determined. An example from a macular angiogram is shown in FIG. 20C. The vitreous or outer retinal flow index can be used to indicate the RNV or CNV flow within the scanned area (3×3 or 6×6 mm) of the vitreous or outer retina. The retinal or choroidal neovascularization area was the area occupied by vessels in the vitreous or outer retina. To identify and quantify the capillary dropout of the inner retina or choriocapillaris, the non-perfusion map was created by identifying decorrelation values lower than a set cutoff point, typically 2.33 standard deviations below the mean according to the normal distribution. Morphologic operations were then used to remove areas below a certain size to reduce noise. The remaining areas were then summed and converted from pixels to metric units.

Results:

Retinal and Choroidal Microcirculation in Normal Subjects:

The retina and choroid are two distinct vascular beds. The 3D nature of OCT angiography allows separate visualizations of these two circulations from the same volumetric scan. In healthy eyes, retinal circulation is located between the internal limiting membrane (ILM) and the outer plexiform layer (OPL), while the choroidal circulation is beneath Bruch's membrane. The vitreous (anterior to the ILM) and outer retina (between OPL and Bruch's membrane) are avascular in normal eyes. One way to present OCT angiography is to use different colors, each representing different vascular beds, superimposed on gray-scale, cross-sectional, structural OCT images (FIG. 19A). Using this technique, both blood flow and retinal structural information are presented on a single image.

En face presentation of OCT angiography is comparable to the traditional view of dye-based angiography and allows clinicians to identify vascular patterns. Segmented en face OCT angiograms can be displayed as individual retinal and choroidal circulations (FIG. 19C, 19E). In healthy eyes, the vitreous and outer retinal layers are colored black (FIG. 19B, 19D), representing the absence of flow.

In vivo imaging of the choroid is limited with current imaging modalities (Mrejen S and Spade R F, *Surv Ophthalmol* 58, 387-429 (2013); incorporated by reference herein). High quality OCT angiograms of the choriocapillaris can be obtained by segmenting a thin slice (10 µm) of the inner choroid below Bruch's membrane (FIG. 19E). The larger and deeper choroidal vessels are more difficult to visualize with SSADA-based OCT angiography. One reason for this is that choriocapillaris flow causes a flow projection artifact in the deeper layers. Selective removal of this artifact is impossible given the near confluent nature of the choriocapillaris. Second, high flow in the larger choroidal vessels reduces the OCT signal due to interference fringe washout. However, visualization of the larger, deeper choroidal vessels is possible using an inverse reflectance display scale (FIG. 19F). This is achieved by taking advantage of the OCT signal void produced by interference fringe washout in regions of very high flow velocity (Hendargo H C et al, *Biomed Opt Express* 2, 2175-2188 (2011); incorporated by reference herein).

Retinal Neovascularization and Capillary Dropout in Diabetic Retinopathy

Diabetic retinopathy is a microangiopathy characterized by capillary occlusion, hyperpermeability, and neovascularization (Frank R N, *N Engl J Med* 350, 48-58 (2004); incorporated by reference herein). These pathophysiologic changes cause proliferative diabetic retinopathy and macular edema, which are responsible for most of the vision loss associated with this disease (Antonetti D A et al, 2012 supra). Assessment of the microvascular changes with FA has been validated as a way to classify disease severity and predict progression (*Ophthalmology* 98, 807-822 (1991); incorporated by reference herein)

Like FA, OCT angiography can visualize areas of low capillary perfusion or dropout. FIG. 20 compares en face retinal OCT angiograms from a normal subject to those from a patient with non-proliferative diabetic retinopathy (NPDR). The central 0.6-mm circle encompasses the normal foveal avascular zone (FAZ), and areas of capillary loss are represented by dark areas elsewhere in the macula. No dark areas are present outside of the FAZ in the normal subject (FIG. 20B, top panel, 20C top panel, 20D top panel), whereas the patient with NPDR has enlargement of the normal FAZ and extensive loss of the macular capillary bed (FIG. 20B bottom panel). Nonperfusion areas on FA correspond to those on OCT angiography (FIG. 20B bottom panel, 20C bottom panel).

SSADA also allows the quantitative evaluation of local circulation by determining the flow index and vessel density in areas of interest, such as the parafoveal and perifoveal areas that correspond respectively to the 3-mm and 6-mm early treatment diabetic retinopathy study (ETDRS) macular fields (as demonstrated in FIGS. 20A-20D). Nonperfusion maps may be created (FIG. 20D) that allows for the area of nonperfusion to be calculated and compared between sequential angiograms.

The development of retinal neovascularization (RNV) signifies progression to the proliferative phase of the disease. Recognition of this change is important because it may guide panretinal photocoagulation and other treatments to reduce the risk of vision loss due to RNV (Ophthalmology 88, 583-600 (1981); incorporated by reference herein). Because OCT angiograms can be segmented by anatomic planes such as the ILM, it can be particularly effective in distinguishing between intra-retinal microvascular abnormalities, which occur in the same plane as the retinal blood vessels, and early RNV, which develops anterior to the retinal vessels and may extend into the vitreous cavity (FIG. 21A-21D). The extent and activity of RNV can also be quantified on OCT angiography by vessel area and flow index. Thus, compared to FA, OCT angiography has the advantages of 3D localization and quantification.

Choroidal Neovascularization in Age-Related Macular Degeneration

Choroidal neovascularization (CNV), the hallmark pathologic feature of neovascular AMD, consists of abnormal blood vessels that grow from the choriocapillaris and penetrate through Bruch's membrane into the sub-retinal pigment epithelium (RPE) space and subretinal space. Subsequent exudation and hemorrhage damage retinal tissue, resulting in vision loss (Ambati J et al, 2003 supra) FA is the gold standard for CNV diagnosis; (Hee M R et al, 1996 supra) however it is limited by its 2D nature. In addition, blocked fluorescence from the RPE or hemorrhage (if present) reduces visibility of the CNV beneath the RPE, as well as visualization of the choroid (Gass J, *Stereoscopic atlas of macular diseases: diagnosis and management, St. Louis, Mosby* ed 24-26 (1997) OCT angiography has the capability to generate 3D angiograms of the retina, choroid, and CNV that is otherwise obscured in FA by RPE blockage or hemorrhage.

In an example of neovascular AMD (FIG. 22A), the late FA image (FIG. 22B) shows a stippled hyperfluoresence leakage pattern, indicating the presence of an occult CNV. The outer retina is devoid of blood flow in healthy eyes, and the flow detected in this area is associated with the presence of CNV. Color-coded composite en face OCT angiography allows for 3D representation of retinal flow, outer retinal flow, and choroidal flow on a single 2D image. In this case, the CNV is highlighted in yellow, and the extent and microvascular structure (FIG. 22C) is better defined compared to traditional FA image (FIG. 22B). The cross-sectional structural OCT image with a color-coded OCT angiogram overlay (FIG. 22D) demonstrates the depth of the CNV, in this case beneath the RPE, as well as the presence of fluid exudation and disruption of outer retinal anatomy.

This case illustrates the capability of OCT angiography to assess the morphology, extent, and depth of CNV in AMD. It has been demonstrated that OCT angiography can be used to classify CNV as type I (between the RPE and Bruch's membrane, FIG. 22D), type II (above the RPE), type III (in the inner retina), or a combined type (Jia et al, 2014A supra). OCT angiography can furthermore provide quantitative data regarding CNV flow and area. These capabilities may prove to be valuable in the assessment of disease severity and monitoring of the effectiveness of treatment. It is likely that, in many cases, CNV growth through Bruch's membrane occurs before the onset of exudation and visual symptoms. While visual acuity at presentation is strongly predictive of the post-treatment outcome, (Ying G et al, *Opththalmology* 120, 122-129 (2013); incorporated by reference herein) OCT angiography may enable the detection of CNV prior to the development of symptoms or detectable changes with structural OCT or FA. Since it is a safe, noninvasive, and rapid imaging technique, at-risk patients may benefit from OCT angiography screening.

Choriocapillaris Loss in Age-Related Macular Degeneration

The choriocapillaris has been implicated in the progression of AMD. In advanced non-neovascular AMD, geographic atrophy (GA) is associated with loss of photoreceptors, RPE, and the choriocapillaris. Whether the RPE or choriocapillaris alterations are the primary event in pathogenesis has been a matter of debate (Bhutto I and Lutty G, *Mol Asp Med* 33, 295-317 (2012); incorporated by reference herein). Histologic studies have described choriocapillaris dysfunction in the intermediate stage of AMD, prior to development of GA or choroidal neovascularization (McLeod D S et al, *Inv Ophthalmol Vis Sci* 50, 4982-4991 (2009); incorporated by reference herein). While efforts have been made to assess the choriocapillaris in vivo, (Mullins R F et al, *Inv Ophthalmol Vis Sci* 52, 1606-1612 (2011); incorporated by reference herein) its small size, high density, and high permeability have made it difficult for conventional imaging modalities, including FA and ICG, to provide meaningful assessment. By segmenting a layer extending 10 μm posterior to Bruch's membrane, OCT angiography provides qualitative and quantitative evaluation of the choriocapillaris, which may be valuable in understanding its role in AMD.

OCT angiography can elucidate the state of the choriocapillaris in GA (FIGS. 23A-23H). In a patient with perifoveal GA, the fundus photograph (FIG. 23A) and autofluorescence image (FIG. 23B) show the affected region. The drusen-RPE complex thickness map (the axial distance from the apex of the drusen and the RPE layer to BM, (FIG. 23C) shows an area of RPE loss corresponding to the clinically evident GA. The choriocapillaris is absent in most of the area correlating to clinical GA (FIG. 23E, 23F). In some areas near the border of the GA with RPE loss, intact choriocapillaris flow is present (FIG. 23G, 23H). In this area of preserved choriocapillaris and slightly beyond it, the outer nuclear layer is also preserved; however, in most of the GA area, the outer nuclear layer, photoreceptors, and RPE are absent.

Choriocapillaris Loss in Choroideremia:

Pathology of the choriocapillaris has been implicated in many disease processes apart from AMD, including those with genetic, inflammatory, and infectious etiologies. Choroideremia is an X-linked recessive chorioretinal dystrophy associated with mutation of the CHM gene. This gene encodes the Rab escort protein 1 (REP-1) and is characterized by significant atrophy of the RPE and choriocapillaris with photoreceptor loss (Coussa R G and Traboulsi E I et al, *Ophthalmic Genet* 33, 57-65 (2012); incorporated by reference herein). Effected patients typically experience night blindness in their first or second decade, followed by constriction of the peripheral visual fields until central vision is lost. Patients with choroideremia often demonstrate retinal vessels of normal caliber until late in the disease, suggesting a relatively greater loss of choroidal blood flow. Spectral-domain OCT studies of patients with choroideremia show photoreceptor rosettes, suggesting loss of RPE prior to that of photoreceptors. However, the temporal relationship of RPE loss versus choriocapillaris loss is unknown.

OCT angiography with SSADA may aid in understanding the disease pathogenesis and inform the debate on whether degeneration occurs first in the choriocapillaris, RPE, or photoreceptors. En face OCT angiography has the ability to map both retinal and choroidal perfusion down to the capillary level. In the 3 subjects with choroideremia, OCT angiography (FIG. 24A-24E) showed that the choriocapillaris nonperfusion area was more extensive than the retinal nonperfusion in all cases. The area of RPE loss was even more extensive than choriocapillaris nonperfusion. These patterns suggest that RPE loss might be the primary event, with subsequent choroidal perfusion loss following more closely than retinal perfusion loss. With the recent initiation of gene therapy trials, (MacLaren R E et al, *Lancet* 383, 1129-1137 (2014); incorporated by reference herein) the ability to quantify and map both choroidal and retinal circulations may prove valuable in assessing disease severity and response to treatment.

Example 4—Optical Coherence Tomography Angiography Image Processing System

FIG. 25 schematically shows an example system 100 for OCT image processing in accordance with various embodiments. System 100 comprises an OCT system 102 configured to acquire an OCT image comprising OCT interferograms and one or more processors or computing systems 104 that are configured to implement the various processing routines described herein. OCT system 100 can comprise an OCT system suitable for OCT angiography applications, e.g., a swept source OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., the method depicted in FIGS. 1-4 described above, can be implemented as a computer application, computer service, computer API, computer library, and/or other computer program product.

FIG. 26 schematically shows a non-limiting computing device 200 that can perform one or more of the above described methods and processes. For example, computing device 200 can represent a processor included in system 100 described above, and can be operatively coupled to, in communication with, or included in an OCT system or OCT image acquisition apparatus. Computing device 200 is shown in simplified form. It is to be understood that virtually any computer architecture can be used without departing from the scope of this disclosure. In different embodiments, computing device 200 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 200 includes a logic subsystem 202 and a data-holding subsystem 204. Computing device 200 can optionally include a display subsystem 206, a communication subsystem 208, an imaging subsystem 210, and/or other components not shown in FIG. 26. Computing device 200 can also optionally include user input devices such as manually actuated buttons, switches, keyboards, mice, game controllers, cameras, microphones, and/or touch screens, for example.

Logic subsystem 202 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 204 can include one or more physical, non-transitory, devices configured to hold data and/or instructions executable by the logic subsystem to implement the herein described methods and processes. When such methods and processes are implemented, the state of data-holding subsystem 204 can be transformed (e.g., to hold different data).

Data-holding subsystem 204 can include removable media and/or built-in devices. Data-holding subsystem 204 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 204 can include devices with one or more of the following characteristics: volatile, nonvolatile, dynamic, static, read/write, read-only, random access, sequential access, location addressable, file addressable, and content addressable. In some embodiments, logic subsystem 202 and data-holding subsystem 204 can be integrated into one or more common devices, such as an application specific integrated circuit or a system on a chip.

FIG. 26 also shows an aspect of the data-holding subsystem in the form of removable computer-readable storage media 212, which can be used to store and/or transfer data and/or instructions executable to implement the herein described methods and processes. Removable computer-readable storage media 212 can take the form of CDs, DVDs, HD-DVDs, Blu-Ray Discs, EEPROMs, flash memory cards, USB storage devices, and/or floppy disks, among others.

When included, display subsystem 206 can be used to present a visual representation of data held by data-holding subsystem 204. As the herein described methods and processes change the data held by the data-holding subsystem, and thus transform the state of the data-holding subsystem, the state of display subsystem 206 can likewise be transformed to visually represent changes in the underlying data. Display subsystem 206 can include one or more display devices utilizing virtually any type of technology. Such display devices can be combined with logic subsystem 202 and/or data-holding subsystem 204 in a shared enclosure, or such display devices can be peripheral display devices.

When included, communication subsystem 208 can be configured to communicatively couple computing device 200 with one or more other computing devices. Communication subsystem 208 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 200 to send and/or receive messages to and/or from other devices via a network such as the Internet.

When included, imaging subsystem 210 can be used acquire and/or process any suitable image data from various sensors or imaging devices in communication with computing device 200. For example, imaging subsystem 210 can be configured to acquire OCT image data, e.g., interferograms, as part of an OCT system, e.g., OCT system 102 described above. Imaging subsystem 210 can be combined with logic subsystem 202 and/or data-holding subsystem 204 in a shared enclosure, or such imaging subsystems can comprise periphery imaging devices. Data received from the imaging subsystem can be held by data-holding subsystem 204 and/or removable computer-readable storage media 212, for example.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

The invention claimed is:

1. A method of visualizing choroidal neovascularization, the method comprising:

receiving a set of cross-sectional optical coherence tomography (OCT) angiograms;

segmenting the set of cross-sectional OCT angiograms using OCT structural images into an en face inner retina angiogram and a first en face outer retina angiogram;

removing a flow projection artifact from the first en face outer retina angiogram, thereby producing a second en face outer retina angiogram;

generating a color-coded composite en face angiogram from the en face inner retina angiogram and the first en face outer retina angiogram;

removing a flow projection artifact from the set of cross-sectional OCT angiograms using the second en face outer retina angiogram;

generating a color-coded composite cross-sectional angiogram from the set of cross-sectional OCT angiograms to provide a visualization of classifying choroidal neovascularization (CNV) by type on the basis of an outer retinal flow and a position relationship to the retinal pigment epithelial (RPE) using the composite cross-sectional angiogram.

2. The method of claim 1, further comprising applying a filter to the second en face outer retina angiogram.

3. The method of claim 2 wherein the filter comprises a Gaussian filter or a low pass filter.

4. The method of claim 2, further comprising detecting CNV in the second en face outer retina angiogram using pattern recognition, thereby generating a masked outer retina angiogram.

5. The method of claim 4, further comprising generating a third en face outer retina angiogram based on the masked outer retina angiogram.

6. The method of claim 5, further comprising wherein the set of cross-sectional OCT angiograms are further segmented into an en face choroid angiogram.

7. The method of claim 6, further comprising assigning a first color to blood flow detected in the en face inner retina angiogram, assigning a second color to blood flow detected in the en face choroid angiogram, and assigning a third color to blood flow detected in the third en face outer retina angiogram.

8. The method of claim 6, further comprising using the third en face outer retina angiogram to remove projection artifacts in the cross-sectional angiogram of the outer retina.

9. The method of claim 8, further comprising assigning the first color to blood flow detected in the inner retina cross-sectional angiogram, assigning the second color to blood flow detected in the choroid cross-sectional angiogram, and assigning the third color to blood flow in the cross-sectional outer retina angiogram.

10. The method of claim 6, further comprising overlaying the en face inner retina angiogram, the en face choroid angiogram, and the third en face outer retina angiogram to create a composite en face angiogram.

11. The method of claim 1, comprising scanning a subject using an OCT angiography protocol and processing the data from the scan, thereby generating the set of cross-sectional OCT angiograms.

12. The method of claim 11, wherein the OCT angiography protocol comprises a split-spectrum amplitude decorrelation algorithm (SSADA).

13. The method of claim 1, further comprising determining a CNV area and a flow index.

14. The method of claim 13, wherein the CNV area is determined by summing a number of pixels for which a decorrelation value is above a background value.

15. The method of claim 14, further comprising converting the sum of the number of pixels to physical dimensions.

16. The method of claim 14, wherein determining the flow index comprises summing the decorrelation value of the pixels that encompass the CNV and then dividing by an area of the en face outer retina angiogram.

* * * * *